US006943021B2

(12) United States Patent
Klausner et al.

(10) Patent No.: US 6,943,021 B2
(45) Date of Patent: Sep. 13, 2005

(54) THREE DIMENSIONAL VAGINAL TISSUE MODEL CONTAINING IMMUNE CELLS

(75) Inventors: Mitchell Klausner, Sharon, MA (US); Seyoum Ayehunie, Natick, MA (US); Joseph Kubilus, Dracut, MA (US)

(73) Assignee: MatTek Corporation, Ashland, MA (US)

( * ) Notice: Subject to any disclaimer, the term of this patent is extended or adjusted under 35 U.S.C. 154(b) by 426 days.

(21) Appl. No.: 10/165,267

(22) Filed: Jun. 7, 2002

(65) Prior Publication Data

US 2003/0228686 A1 Dec. 11, 2003

(51) Int. Cl.[7] ............................................... C12N 5/00
(52) U.S. Cl. ...................... 435/373; 424/93.7; 435/377
(58) Field of Search ..................... 424/93.7; 435/373, 435/377

(56) References Cited

U.S. PATENT DOCUMENTS

| | | | |
|---|---|---|---|
| 4,963,489 A | 10/1990 | Naughton et al. | 435/240.1 |
| 5,032,508 A | 7/1991 | Naughton et al. | 435/32 |
| 5,160,490 A | 11/1992 | Naughton et al. | 435/284 |
| 5,266,480 A | 11/1993 | Naughton et al. | 435/240.243 |
| 5,443,950 A | 8/1995 | Naughton et al. | 435/1 |
| 5,478,739 A | 12/1995 | Slivka et al. | 435/240.23 |
| 5,512,475 A | 4/1996 | Naughton et al. | 435/240.243 |
| 5,516,680 A | 5/1996 | Naughton et al. | 435/240.243 |
| 5,516,681 A | 5/1996 | Naughton et al. | 435/240.243 |
| 5,518,915 A | 5/1996 | Naughton et al. | 435/240.243 |
| 5,541,107 A | 7/1996 | Naughton et al. | 435/240.243 |
| 5,578,485 A | 11/1996 | Naughton et al. | 435/240.243 |
| 5,580,781 A | 12/1996 | Naughton et al. | 435/240.243 |
| 5,627,025 A | 5/1997 | Steinman et al. | |
| 5,698,436 A | 12/1997 | Morgan et al. | 435/240.2 |
| 5,750,397 A | 5/1998 | Tsukamoto et al. | 435/372 |
| 5,763,197 A | 6/1998 | Tsukamoto et al. | 435/7.21 |
| 5,766,944 A | 6/1998 | Ruiz | |
| 5,785,964 A | 7/1998 | Naughton et al. | 424/93.21 |
| 5,830,682 A | 11/1998 | Moore | 435/29 |
| 5,858,721 A | 1/1999 | Naughton et al. | 435/69.1 |
| 5,861,153 A | 1/1999 | Schmidt et al. | 424/93.7 |
| 5,962,325 A | 10/1999 | Naughton et al. | 435/395 |
| 5,968,546 A | 10/1999 | Baur et al. | 424/444 |
| 6,022,743 A | 2/2000 | Naughton et al. | 435/395 |

OTHER PUBLICATIONS

Delvenne et al., Vaccine 19: 2557–2564 (2001).*
Aebischer, F. et al. "Organotypic raft cultures for the in vitro evaluation of vaginal microbicidal agents", Sex. Trans. Dis., 24: 69–76 (1997).
Ayehunie, S. et al. "Reconstruction of vaginal tissue model for HIV infection", Abstract and presentation materials for Nobel Symposium #119: *Global HIV therapeutics—HIV vaccines* Stockholm, Sweden (Jun. 7–9, 2001).
Ayehunie, S. et al., "In vitro reconstructed ectocervical–vaginal tissue model", Abstract and presentation materials for 2nd Annual Harvard Medical School Centers for AIDS Research Symposium: International Efforts in HIV/AIDS Treatment and Prevention (Mar. 4, 2002).
Bernstam, L.I. et al., "Keratinocytes grown at the air–liquid interface", *In Vitro Cellular & Development Biology*, 22 (12):695–705 (1986).
Blauvelt, A., "The role of skin dendritic cells in the initiation of Human Immunodeficiency Virus infection", Am. J. Med., 102 (5B): 16–20 (1997).
Boyce, S.T. et al., "Calcium–regulated differentiation of normal human epidermal keratinocytes in chemically defined clonal culture and serum–free serial culture", *Journal of Investigative* Dermatology, 81:33s–40s (1983).
Buchanan, D.L. et al., "Role of stromal and epithelial estrogen receptors in vaginal epithelial proliferation, stratification, and cornification", Endocrinol., 139(10):4345–4352 (1998).
Cameron, P. et al., "Dendritic cells and the replication of HIV–1", *J. Leukocyte Biol.*, 59: 158–171 (1996).
Cannon, C.L. et al., "New epidermal model for dermal irritancy testing", *Toxic. in Vitro*, 8(4):889–891 (1994).
Caux, C. et al., "GM–CSF and TNF–α cooperate in the generation of dendritic Langerhans cells", Nature, 360:258–261 (1992).
Cohen, M.S., "Sexually transmitted diseases enhance HIV transmission: no longer a hypothesis", Lancet, 351 (suppl III):sm5–sm7 (1998).

(Continued)

*Primary Examiner*—Jean C. Witz
(74) *Attorney, Agent, or Firm*—Lowris, Lando & Anastani, LLP

(57) ABSTRACT

Disclosed is a cervico-vaginal tissue equivalent comprised of vaginal epithelial cells and immune cells, cultured at the air-liquid interface. The tissue equivalent is capable of being infected with a sexually transmitted pathogen such as a virus (e.g., HIV), a bacteria, a helminthic parasite, or a fungus. The tissue equivalent is also capable of undergoing an allergic-type reaction or an irritant-type reaction. The tissue equivalent is characterized as having nucleated basal layer cells and nucleated suprabasal layer cells, and further as having cell layers external to the suprabasal layer progressively increasing in glycogen content and progressively decreasing in nuclei content. Immune cells of the tissue equivalent are primarily located in the basal and suprabasal layers. Also disclosed are methods for producing the tissue equivalent. The methods involve providing vaginal epithelial cells and immune cells, seeding the cells onto a porous support, and co culturing the seeded cells at the air-liquid interface under conditions appropriate for differentiation. One such method disclosed is for generation of the tissue equivalent in serum free medium. Specific cells from which the tissue equivalent is generated, and also specific preferred components of the medium in which the tissue equivalent is generated are provided. Also disclosed is a cervico-vaginal tissue equivalent produced by the methods disclosed herein.

31 Claims, 2 Drawing Sheets

OTHER PUBLICATIONS

Collins, K.B. et al., "Development of an in vitro organ culture model to study transmission of HIV–1 in the female genital tract", Nature Medicine, 6: 475–479 (2000).

Conti, C.J. et al. "Regulation of cultured rat vaginal epithelial cells by 17β–estradiol and progesterone", J. Steroid Biochem., 24(3):747–751 (1986).

Doillon, C.J. et al., "Method of growing vaginal mucosal cells on a collagen sponge matrix", J. Reproduct. Med., 35(3):203–207 (1990).

Esche, C. et al., "Differential regulation of epidermal and dermal dendritic cells by IL–12 and Flt3 ligand", J. Invest. Dermatol., 113(6):1028–1032 (1999).

Furuta, Y. et al., "Infection of vaginal and colonic epithelial cells by the human immunodeficiency virus type 1 is neutralized by antibodies raised against conserved epitopes in the envelope glycoprotein gp120", Proc. Natl. Acad Sci. USA, 91: 12559–12563 (1994).

Granelli–Piperno, A. et al., "Virus replication begins in dendritic cells during the transmission of HIV–1 from mature dendritic cells to T–cells", Curr. Biol., 9:21–29 (1999).

Greenhead, P. et al,. "Parameters of human immunodeficiency virus infection of human cervical tissue and inhibition by vaginal virucides", J. of Virol., 74(12):5557–5586 (2000).

Howell, A.L. et al., "Human immunodeficiency virus type 1 infection of cells and tissues from the upper and lower human female reproductive tract", J. Virol., 71:3498–3506 (1997).

Hu, J. et al., "Immunophenotypic characterization of simian immunodeficiency virus–infected dendritic cells in cervix, vagina, and draining lymph nodes of the rhesus monkeys", Lab. Invest., 78: 435–451 (1998).

Iguchi, T. et al., "Growth of mouse vaginal epithelial cells in culture: effect of sera and supplemented serum–free medium", In Vitro Cell. Dev. Biol., 23(8):535–540 (1987).

Kawamura, T., et al., "Candidate microbicides block HIV–1 infection of human immature Langerhans cells within epithelial tissue explants," J. Exp. Med., 192 (10):1491–1500 (2000).

Klausner, M., et al., "Intra– and interlaboratory reproducibility of epiderm, an in vitro model for dermal irritancy testing", In *Advances in Animal Alternatives for Safety and Efficacy Testing*, eds. Salem, H., Katz, S.A., Taylor & Francis, Washington, DC, pp. 347–357 (1997).

Klausner, M., et al., "Human tissue model for heterosexual HIV infection" Abstract, Grant No. 1R43AI047792–01, Retrieved from the Internet: http://crisp.cit.nih.gov .

Mells, G.B., et al., "[Role of pH as a regulator of vaginal physiological environment]", Minerva Ginecol., 52(4):111–121 (2000) [Italian. Abstract only.].

Meyers, C. et al., "Biosynthesis of human papillomavirus from a continuous cell line upon epithelial differentiation", Science 257:971–973 (1992).

Mosmann, T., "Rapid colorimetric assay for cellular growth and survival: application to proliferation and cytotoxicity assays", J. Immunol. Meth. 65(1–2):55–63 (1983).

Ozawa, S. et al., "Effect of certain growth factors on proliferation in serum–free collagen gel culture of vaginal epithelial cells from prepuberal mice exposed neonatally to diethylstilbestrol", Proc. Soc. Exper. Biol. Med., 198:760–763 (1991).

Phillips, D.M. et al., "Mechanism of monocyte–macrophage–mediated transmission of HIV", AIDS Res. Hum. Retroviruses, 14 Suppl 1.:S67–70 (1998).

Shattock, R.J. et al., "In vitro models of mucosal HIV transmission", Nature Medicine, 6(6):607–608 (2000).

SkinEthic Laboratories, "Reconstituted human vaginal epithelium", retrieved from the Internet: http://perso.wanadoo.fr/skinethic/Vaginal%20Epithelium.htm [Online publication date unknown].

Sobel, J.D. et al., "Human vaginal epithelial multilayer tissue culture", In Vitro, 15 (12):993–1000 (1979).

Sobel, J.D. et al., "Comparison of bacterial and fungal adherence to vaginal exfoliated epithelial cells and human vaginal epithelial tissue culture cells", Infection and Immunity, 35(2):697–701 (1982).

Stern, M. et al., "Evaluation of the EpiOcular™ tissue model as an alternative to the Draize eye irritation test", Toxicology In vitro, 12:455–459, 461 (1998).

Suemoto, Y. et al., "IL–12 promotes the accessory cell function of epidermal Langerhans cells", J. Dermatol. Sci., 18:98–108 (1998).

Tan, X. et al., "Cell–mediated infection of cervix derived epithelial cells with primary isolates of human immunodeficiency virus", Arch. Virol., 141:1177–89 (1996).

Tsai, P–S. et al., "Proliferation and differentiation of prepubertal mouse vaginal epithelial cells in vitro and the specificity of estrogen–induced growth retardation", In Vitro Cell. Dev. Biol, 27A:461–468 (1991).

Wieser, F. et al., "Progesterone increases the number of Langerhans cells in human vaginal epithelium", Fertil Steril., 75(6):1234–1235 (2001).

Zaitseva, M. et al., "Expression and function of CCR5 and CXCR4 on human Langerhans cells and macrophages: implications for HIV primary infection", Nature Med., 3(12):1369–1375 (1997).

Zambruno,G. et al., "Langerhans cells and HIV–1 infection", Immunol. Today, 16:520–524 (1995).

Zhu, T., "Genotypic and phenotypic characterization of HIV–1 in patients with primary infection", Science, 261(5125):1179–81 (1993).

Greenhead, et al., *Parameters of Human Immunodeficiency Virus Infection of Human Cervical Tissue and Inhibition of Vaginal Virucides*, Journal of Virology, Jun. 2000, pp. 5577–5586, vol. 74, No. 12.

Fichorova, et al., *Generation of Papillomavirus–Immortalized Cell Lines From Normal Human Ectocervical, Endocervical, and Vaginal Epithelium That Maintain Expression to Tissue–Specific Differentiation Proteins*, Biology Reproduction, 1997, pp. 847–855, vol. 57, No. 4.

International Search Report, filed May 32, 2003, Application No. PCT/US03–16167.

* cited by examiner

THREE DIMENSIONAL VAGINAL TISSUE MODEL CONTAINING IMMUNE CELLS

GOVERNMENT FUNDING

Work described herein was supported under SBIR Grant 1R43 AI047792-01, awarded by the National Institutes of Health. The U.S. government therefore may have certain rights in this invention.

BACKGROUND OF THE INVENTION

A number of in vitro model systems have been used to study the effects of exogenous and endogenous agents on vaginal tissue. Although useful, each model system developed to date has suffered from significant drawbacks.

Vaginal epithelial cells in monolayer culture have been used for basic biochemistry studies and to determine the effects of hormones, growth factors and exogenous agents on cervical and vaginal tissue. Others have used monolayer cultures of cervical or vaginal cells, in conjunction with blood derived dendritic cells and T-cells in suspension culture, to investigate the mechanism of infection involved in sexually transmitted diseases. However, cells in monolayer culture lack the differentiated function and barrier properties of cells found in normal tissue. Hence results with monolayer or suspension cells may not apply to normal human cervical-vaginal tissue.

A three dimensional tissue produced from cultured skin keratinocytes has also been used to study the effects of vaginal microbicidal agents. Although useful, due to the skin origin of the cells, the tissue is not fully representative of in vivo cervical and vaginal tissue, and thus its use as a vaginal tissue model is severely limited.

Multi-layered organ cultures of vaginal tissue explants were reported by Sobel et al. (Sobel, J. D., et al., *In vitro*, 15, 993–1000 (1979)) as early as 1979 when non-malignant vaginal tissues were cultured on glass slides. Other studies have used epithelial cell outgrowths from cervical and vaginal tissue explants to study pathogenesis of the in vivo tissue and the efficacy of microbicidal agents at preventing infection. However, the availability of normal (non-cancerous) human vaginal and cervical tissue is limited, and the inability to store such tissue for long periods, make organ cultures usable only in small academic research environments. Also, tissue explants are difficult to handle and manipulate and the problem of tissue by-pass is hard to avoid. For example, it is difficult to insure that applied agents do not circumnavigate the tissue by diffusing around the tissue edges.

In recent years, there has been a growing awareness that the experimental use of vaginal and cervical tissue may further be critical to the study of HIV infection. A number of studies have suggested that Langerhans cells found in the vaginal epithelium, which express CD4 receptors and other co-receptors, are the initial target for HIV-1 infection, and that infected Langerhans cells transmit HIV to CD4$^+$ T-cells (Cohen, M. S., *Lancet*, 351 (supp III), 5–7 (1998)). Langerhans cells have also been shown to be important reservoirs for HIV/SIV replication in vivo (Hu, J., et al., *Lab. Invest.*, 78, 435–451 (1998)). However, studies, such as those which indicate that HIV replication only occurs in the presence of T-cells (Granelli-Piperno, A., Steinman, R. M., et al., *Curr. Biol.*, 14, 21–29 (1999).), and reports of direct HIV-1 infection of ectocervical-vaginal cells which are CD4$^-$ (Tan, X., Phillips, D. M., *Arch. Virol.*, 141, 1177–89 (1996)), preserve controversy as to the role of Langerhans cells in HIV infection.

Development of an in vitro model system that is highly reflective of in vivo cervical and vaginal tissue would greatly facilitate the accurate determination of the effects of exogenous and endogenous agents on vaginal tissue and also the pathogenesis and prevention of sexually transmitted diseases.

SUMMARY OF THE INVENTION

In one aspect, the present invention relates to a cervico-vaginal tissue equivalent comprised of vaginal epithelial cells, and immune cells, cultured at the air-liquid interface. The cervico-vaginal tissue equivalent may optionally be generated in serum free medium. The vaginal epithelial cells, the immune cells, or both, may be of human origin. The vaginal epithelial cells, the immune cells, or both, may be primary cells, passaged primary cells, transformed cells, or immortalized cells. The primary or passaged primary vaginal epithelial cells of the cervico-vaginal tissue equivalent may be derived from normal human ectocervical tissue, normal human endocervical tissue, pathological human ectocervical tissue, or pathological human endocervical tissue. The immune cells of the cervico-vaginal tissue equivalent may be Langerhans cells, Langerhans precursor cells (CD34+), monocytes (CD14+), immature dendritic cells (CD1a+, CD4+), mature dendritic cells (CD86+, HLA-DR++), T cells (CD3+), macrophages, or any combination thereof. The immune cells of the cervico-vaginal tissue equivalent express HLA-DR. The immune cells may be generated in vitro, for instance, from Langerhans precursor cells or monocytes.

In another embodiment, the cervico-vaginal tissue equivalent is capable of being infected with a sexually transmitted pathogen selected from the group consisting of a virus (e.g., HIV), a bacteria, a helminthic parasite, and a fungus. The cervico-vaginal tissue equivalent also may be capable of undergoing an allergic-type reaction or an irritant-type reaction.

The cervico-vaginal tissue equivalent may further comprise a support on which it is cultured. The support may be, for instance, an artificial membrane, an extracellular matrix component, a collagen mixture, in vivo derived connective tissue, a mixed collagen-fibroblast lattice, mixed extracellular matrix-fibroblast lattice, or plastic. The mixed collagen-fibroblast lattice may optionally be comprised of vaginal fibroblasts, and may optionally be further comprised of T cells (CD3+).

The cervico-vaginal tissue equivalent may also be characterized as having nucleated basal layer cells and nucleated suprabasal layer cells. The cervico-vaginal tissue equivalent may further be characterized as having cell layers external to the suprabasal layer progressively increasing in glycogen content and progressively decreasing in nuclei content. The cervico-vaginal tissue equivalent may also be characterized as having immune cells primarily located in the basal and suprabasal layers.

Another aspect of the present invention relates to a method for producing a cervico-vaginal tissue equivalent. The method comprises the steps of providing vaginal epithelial cells and immune cells, seeding the cells, and co-culturing the seeded cells at the air-liquid interface under conditions appropriate for differentiation. The co-culturing step may be in serum free differentiation medium. The method optionally further comprises the step of co-cultivating the seeded cells submerged in growth medium under conditions appropriate for cell propagation, prior to the co-culturing step. The growth medium of the co-cultivating step may be serum free growth medium.

The method for producing a cervico-vaginal tissue equivalent may further comprise the step of culturing the vaginal epithelial cells submerged in growth medium under conditions appropriate for cell propagation, prior to the seeding step. Alternatively, or in addition, the method may further comprise the step of further seeding additional immune cells into the co-cultured seeded cells after the co-culturing step, and further co-culturing the seeded cells at the air liquid interface, under conditions appropriate for differentiation.

The vaginal epithelial cells, the immune cells, or both, used in the above method may be primary cells, passaged primary cells, transformed cells, or immortalized cells. The vaginal epithelial cells, the immune cells, or both, used in the method may also be of human origin. The primary or passaged primary vaginal epithelial cells of the cervico-vaginal tissue equivalent may be derived from normal human ectocervical tissue, normal human endocervical tissue, pathological human ectocervical tissue, or pathological human endocervical tissue. The immune cells of the cervico vaginal tissue equivalent may be Langerhans cells, Langerhans precursor cells (CD34+), monocytes (CD14+), immature dendritic cells (CD1a+, CD4+), mature dendritic cells (CD86+, HLA-DR++), T cells (CD3+), macrophages, or any combination thereof. In one embodiment, the immune cells of the providing step are generated from Langerhans precursor cells or monocytes.

In another embodiment, the seeding step of the method is on an underlying support which may be an artificial membrane, an extracellular matrix component, a collagen mixture, in vivo derived connective tissue, a mixed collagen-fibroblast lattice, mixed extracellular matrix-fibroblast lattice, or plastic. The mixed collagen-fibroblast lattice may be comprised of vaginal fibroblasts, and may further be comprised of T cells (CD3+).

The co-culturing step may be in differentiation medium comprising at least one of the following components: adenine, α-melanocyte stimulating hormone, arachidonic acid, β-fibroblast growth factor, bovine pituitary extract, bovine serum albumin, calcium chloride, calf serum, carnitine, cholera toxin, dibutyl cyclic adenosine monophosphate, endothelin-1, epidermal growth factor, epinephrine, estradiol, estrogen, ethanolamine, fetal bovine serum, FLT-3, glucagon, granulocyte/macrophage-colony stimulating factor, hepatocyte growth factor, horse serum, human serum, hydrocortisone, insulin, insulin-like growth factor 1, insulin-like growth factor 2, interleukin-1β, interleukin-3, interleukin-4, interleukin-6, interleukin-12, interleukin-18, iso-butyl methyl xanthine, isoproterenol, keratinocyte growth factor, linoleic acid, MIP-1α, MIP-3α, newborn calf serum, nor-epinephrine, oleic acid, palmitic acid, phosphoethanolamine, progesterone, stem cell factor, transferrin, transforming growth factor-β1, triiodothyronine, tumor necrosis factor α, vitamin A, vitamin B12, vitamin C, vitamin D, and vitamin E.

In another embodiment of the method, the co-culturing step takes place in differentiation medium comprising a retinoid. The concentration of the retinoid may be, for example, between about $10^{-5}$ M and about $10^{-13}$ M. The retinoid may be retinoic acid. The concentration of the retinoic acid may be, for example, about $5 \times 10^{-10}$ M. In a related embodiment, the differentiation medium is serum free medium, comprising about a 3:1 ratio of DMEM:F12 and about $5 \times 10^{-10}$ M retinoic acid. The serum-free differentiation medium may optionally further comprise about 0.3 ng/ml keratinocyte growth factor, about 5 ng/ml EGF, about 0.4 µg/ml hydrocortisone, and about 5 µg/ml insulin.

In a preferred embodiment of the method, the seeding step is at a ratio of about 1:1 vaginal epithelial cells to immune cells. In another embodiment, the seeding step of the method is at a ratio of between about 1:1 and 10,000:1 vaginal epithelial cells to immune cells, and the co-culturing step is in serum-free medium supplemented with additives which increase viability or induce proliferation of the immune cells. In a preferred embodiment, the ratio is from about 20:1 to about 50:1 vaginal epithelial cells to immune cells and the co-culturing step is in serum-free medium supplemented with additives which increase viability or induce proliferation of the immune cells.

In one embodiment of the method, from about $1 \times 10^3$ to about $1 \times 10^7$ cells/cm$^2$ of each cell type are seeded in the seeding step. Preferably, about $1 \times 10^5$ to about $1 \times 10^6$ cells/cm$^2$ of each cell type are seeded in the seeding step.

The immune cells used in the method for producing a cervico-vaginal tissue equivalent may be isolated as immature or mature dendritic cells, prior to the providing step.

In one embodiment, the method for producing a cervico-vaginal tissue equivalent further comprises the step of generating the immune cells for the providing step in vitro from harvested CD34$^+$ cells, prior to the providing step. The step of generating the immune cells from harvested CD34+ cells, may comprise harvesting CD34+ cells from human umbilical cord blood, peripheral blood or bone marrow, initially culturing the CD34+ cells in medium comprising about 25 ng/ml stem cell factor, about 200 U/ml GM-CSF, and about 2.5 ng/ml TNF-α, for a period of from about 1 to about 10 days, and continuing culturing the CD34+ cells in medium comprising about 25 ng/ml stem cell factor, about 200 U/ml GM-CSF, about 40 ng/ml IL-4, and about 0.5 ng/ml TGF-β1 for a period of from about 1 to about 17 days. In one embodiment, the period of the initially culturing step is about 5 to about 10 days, preferably about 7 to about 9 days. Alternatively, the step of generating the immune cells from harvested CD34+ cells, comprises the steps of harvesting CD34+ cells from human umbilical cord blood, peripheral blood or bone marrow, initially culturing the CD34+ cells in serum free medium comprising about 20 ng/ml stem cell factor, about 500 U/ml GM-CSF, and about 2.5 ng/ml TNF-α, for a period of at least about 4 days, continuing culturing the CD34+ cells in serum free medium comprising about 20 ng/ml stem cell factor, about 500 U/ml GM-CSF, about 2.5 ng/ml TNF-α, about 20 ng/ml FLT-3, and about 0.5 ng/ml TGF-β1, for a period of at least about 5 days, and further culturing the CD34+ cells in serum free medium comprising about 20 ng/ml stem cell factor, about 500 U/ml GM-CSF, about 40 ng/ml IL-4, about 20 ng/ml FLT-3, and about 0.5 ng/ml TGF-p 1, for a period of at least about 3 days.

Another aspect of the present invention relates to a cervico-vaginal tissue equivalent produced by the methods described herein. In one embodiment, the method comprises the steps of providing vaginal epithelial cells and immune cells, seeding the cells, and co-culturing the seeded cells at the air-liquid interface under conditions appropriate for differentiation. The method may further comprise the step of co-cultivating the seeded cells submerged in growth medium under conditions appropriate for cell propagation, prior to the co-culturing step.

DETAILED DESCRIPTION OF THE INVENTION

Figure 1:
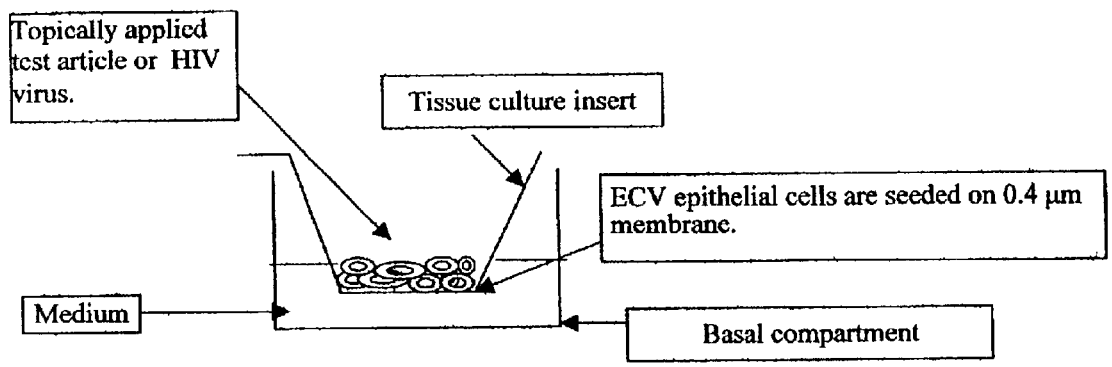
FIG. 1 is a schematic illustration of the ectocervo-vaginal tissue grown at the air liquid interface. Nutrients and growth factors are supplied to the tissue from medium placed in the basal compartment which permeate through the membrane at the bottom of the tissue culture insert. No culture medium is present on the apical tissue surface thereby allowing for topical application of test materials such as pathogens and microbicides.

Aspects of the present invention relate to the development of a three-dimensional cervico-vaginal tissue equivalent described herein. The cervico-vaginal tissue equivalent comprises vaginal and/or cervical epithelial cells derived from in vivo tissue with a three-dimensional cellular organization which strongly reflects the morphology of the in vivo tissue. Similar to the in vivo tissue, the tissue equivalent of the present invention also contains functionally incorporated immune cells, and is immunocompetent. The cervico-vaginal tissue equivalent with these characteristics serves an in vitro model system which more accurately reflects the properties of in vivo vaginal tissue than other known model systems presently available in the art. As such, the cervico-vaginal tissue equivalent can be used to more accurately determine the effects of foreign agents on vaginal tissue and to study the transmission of sexually transmitted disease pathogens.

I. The Cervico-Vaginal Tissue Equivalent

In one aspect the present invention relates to a cervico-vaginal tissue equivalent comprised of both vaginal epithelial cells and immune cells which have been cultured in vitro at the air-liquid interface to produce a three-dimensional tissue which is representative of in vivo vaginal and cervical tissue. The cervico-vaginal tissue equivalent is characterized as having cellular organization, morphology, and histology similar to in vivo vaginal tissue. For instance, in one embodiment, microridges are present on the apical surface of the cervico-vaginal tissue equivalent, and the cells of the tissue found near the apical surface of the tissue are highly interdigitated in a zipper-like pattern. In one embodiment, desmosomes are also present between the cells located in the lower layers of the tissue.

In a preferred embodiment, the cervico-vaginal tissue equivalent of the present invention is characterized as having nucleated basal cells and a number of nucleated suprabasal cell layers, followed by layers more toward the apical surface which lack nuclei and organelles and are filled with glycogen. These morphological characteristics are readily visualized by micrographic analysis.

The presence of glycogen in the outer cell layers is a significant characteristic of a preferred embodiment of the cervico-vaginal tissue equivalent. This is a characteristic of the in vivo tissue that is understood to be lacking in other current model systems known in the art. The presence of glycogen in the apical layers of the in vivo tissue is known to be extremely important in maintaining the normal physiological environment within the vagina since the environment is dependent on several microorganisms naturally resident therein. The predominant vaginal microorganism is Doderlein's lactobacillus which ferments glycogen released from these apical cells to produce lactic acid and thereby stabilizing the pH of the vagina between 4.5–5.0 (Melis, G. B., et al., *Minerva Ginecol.*, 52(4), 111–121 (2000)). Other known in vitro model systems used to study vaginal tissue do not demonstrate the glycogen content of in vivo systems, and of the tissue equivalent of the present invention. Thus, the presence of glycogen indicates that the cervico-vaginal tissue equivalent is a more representative model system than other systems currently available in the art.

The cervico-vaginal tissue equivalent is also similar to in vivo tissue histologically in that it possesses characteristic cellular markers at similar locations to the in vivo tissue. In one embodiment, cellular markers cytokeratin 13 (CK13) and 14 (CK14) are readily identified by immunohistochemical analysis of the tissue equivalent, with CK13 present in the more differentiated suprabasal layers, and CK14 present in the basal layers.

An important aspect of the cervico-vaginal tissue equivalent of the present invention is the presence of incorporated immune cells naturally present in vivo in vaginal tissue. The functional incorporation of immune cells into the tissue equivalent is an important innovation over the model systems of cervical-vaginal tissue of the prior art. This functional presence of the immune cells results in immunocompetence of the tissue. Thus, the tissue possesses functional characteristics of the natural in vivo tissue associated with immunocompetence. Some such characteristics are the ability to undergo an allergic-type reaction and the ability to undergo an irritant-type reaction, when exposed to substances which would trigger said reactions. This ability significantly contributes to the value of the tissue equivalent as a model system for in vivo vaginal tissue.

In a preferred embodiment, the immune cells are primarily located in the basal and suprabasal layers of the tissue equivalent. In one embodiment, greater than 50% of the functional immune cells are located in the basal and suprabasal layers. In another embodiment, greater than 60%, 70%, 80% or 90% of the functional immune cells are located in the basal and suprabasal layers. In addition, the immune cells may be further dispersed throughout any underlying connective tissue present. Thee also may be some immune cells located in other layers of the tissue, believed to be an artifact of the generation process.

The presence of the immune cells within the tissue equivalent is readily determined by the skilled artisan. Such immune cells are, for instance, identified experimentally by the presence of specific cellular markers, such as HLA-DR (Human Leukocyte Antigen) for Langerhans cells.

As known in the art, an allergic-type reaction results from topical contact of an allergenic substance to the tissue. The allergic contact reaction involves initial exposure and processing of an antigen by an antigen presenting cell (APC). Antigens leading to allergic reactions may include proteins, bacteria, microorganisms, or chemicals. The chief antigen presenting cells in the vaginal and cervical tissues are Langerhans cells, though other cells may also process antigens or be involved in the early biochemical phenomena associated with allergic reactions. Once the APCs have processed the antigen, the APC becomes activated and subsequently it interacts with T lymphocytes which become sensitized to the specific antigen. In vivo, this initial exposure results in sensitization which may or may not result in an allergic reaction with clinical symptoms such as inflammation, swelling, redness, itching, soreness, pain, or abnormal vaginal odor vaginal discharge. In vivo and in vitro, upon subsequent exposure to the antigen, sensitized T cells are further activated and other inflammatory cells are recruited, which will cause some or all of these clinical symptoms. The allergic-type reaction for a given antigen is generally specific to a subset of individuals, and as such is expected to be specific to a subset of tissue equivalents, depending upon the origin of the cells from which the equivalent is generated.

The allergic-type reaction mounted by the in vitro tissue equivalent closely resembles the in vivo reaction. Initial in vitro effects may include a reduction in tissue viability, the production and/or release of cytokines involved in the initial stages of an allergic reaction, migration of Langerhans cells from the tissue, activation of T cells, and changes in tissue biochemistry.

As is known in the art, an irritant-type reaction also arises from contact of an irritant substance to the tissue. The irritant-type reaction is a less specific, more localized reaction than an allergic-type reaction, and occurs in most, if not all, individuals contacted with the irritant. Clinically, the irritant-type reaction typically initiates with some disruption or physical damage caused to the epithelial cells of the tissue. The irritant induces inflammation characterized by redness, itching, soreness, pain, swelling, or abnormal vaginal odor or discharge. Although inflammatory cells (T lymphocytes) have a role in the development of the irritation reaction, allergen-specific immune lymphocytes are not involved in the pathogenesis and prior sensitization is not necessary. Susceptibility to irritants varies, but given sufficient exposure, nearly all individuals can develop an irritant-type reaction.

The irritant-type reaction mounted by the in vitro tissue equivalent closely resembles the in vivo reaction. Initial in vitro effects may include a reduction in tissue viability, the production and/or release of cytokines involved in the initial stages of an allergic reaction, abrogation of the tissue barrier function, and changes in tissue biochemistry.

Due to the presence of differentiated cell types representative of the in vivo tissue, the tissue equivalent of the present invention is susceptible to infection by a variety of pathogens which normally infect vaginal and/or cervical tissue (e.g. sexually and non-sexually transmitted disease pathogens) to cause sexually transmitted disease.

The term "sexually transmitted disease" encompasses a large number of sexually transmitted infections. These include, without limitation, Acquired Immunodeficiency Syndrome (AIDS), Acute Urethral Syndrome or Cystitis, Bacterial Vaginosis Vulvovaginitis, Candidiasis, Cervical Intraepithelial Neoplasia, Chancroid, *Chlamydia*, Cytomegalovirus infections, Enteric infections, Genital Warts, *Gonorrhea*, Granuloma Inguinale, Hepatitis B, Herpes Genitalis, Human Papillomavirus (HPV), *Lymphogranuloma venereum* (LGV), Molluscum Contagiosum, Mucopurulent Cervicitis, Nongonococcal Urethritis, Pediculosis Pubis, Pelvic Inflammatory Disease (PID), Syphilis, Trichomoniasis and Vulvovaginitis. A sexually transmitted disease is caused by a sexually transmitted pathogen. These pathogens include viral pathogens, bacterial pathogens, fungal pathogens, and helminthic pathogens.

A number of sexually transmitted viral pathogens are known in the art. For instance Acquired Immunodeficiency Syndrome is caused by Human Immunodeficiency Virus (HIV). Cervical Intraepithelial Neoplasia (CIN) has been associated with human papilloma virus (HPV) and the Herpes Simplex Virus. Cytomegalovirus infections are caused by a DNA virus of the Herpes virus group. Genital Warts are caused by the human papillomavirus (HPV), a small DNA virus which belongs to the papillomavirus group. Herpes Genitalis is caused by the Herpes Simplex II virus (HSV). Hepatitis B is caused by Hepatatis B virus (HBV), a DNA virus with multiple antigenic components. Molluscum Contagiosum is caused by the Molluscum Contagiosum virus, the largest DNA virus of the poxvirus group.

Bacterial pathogens known in the art include, without limitation, Acute Urethral Syndrome which is caused by *E. coli, C. trachomatis, N. gonorrhea* and other gram-negative bacteria. Chancroid is caused by *Hemophilus Ducreyi*. Chlamydia, one of the most common bacterial STD infections in the United States, is caused by *Chlamydia trachomatis*. Gonorrhea is caused by *Neisseria Gonorrhea*, a gram-negative diplococcus. Granuloma Inguinale is caused by the gram-negative bacteria calymmato-bacterium granulomatis. *Lymphogranuloma venereum* (LGV) is caused by immuno-types L I, L II, or L III of *Chlamydia Trachomatis*. Mucopurulent Cervicitis is caused by *Chlamydia* and *Gonorrhea*. Nongonococcal Urethritis (NGU) is caused by *Chlamydia* of the D to K immunotypes. Pelvic Inflammatory Disease (PID) is caused by *Gonorrhea, Chlamydia*, and other anaerobic bacteria and gram-negative rods, such as *E. coli* and mycoplasma homines. Syphilis is caused by *Treponema Pallidum*, a spirochete.

Fungal pathogens include yeasts such as *Candida albicans*. Helminthic infections include protozoa infections by trichomonas *vaginalis* which lead to Trichomonas Vaginalis vaginitis, or vulvovaginitis.

In addition, the tissue equivalent of the present invention is also susceptible to enteric infections, which are related to sexually transmitted diseases. They are caused by many sexually transmissible bacteria, viruses and protozoa, carried in the gastrointestinal tract.

Importantly, the tissue equivalent of the present invention is susceptible to infection with the pathogen HIV. This susceptibility is due to the presence of immune cells within the tissue. Although it has been hypothesized that HIV gained entry by infecting immune cells present within genital tissue, prior to Applicants' discovery, considerable controversy surrounded this hypothesis. The results of experiments detailed in the Examples section below support the hypothesis that HIV gains entry by infecting immune cells in the genital tissue and illustrate the utility of the tissue equivalent in further study of the mechanism of HIV infection. They also illustrate its utility in the development of neutralizing substances effective at treating and preventing the infection.

The cervico-vaginal tissue equivalent of the present invention is intended to encompass tissue which is separated to various degrees from the support on which it was developed. To generate the tissue equivalent, the cells that make up the tissue are cultured on a support which facilitates culture at the air-liquid interface. Depending upon the composition of this support, the support, or components thereof, may be integrally incorporated into the tissue which develops. In one embodiment, the tissue equivalent of the present invention contains the support on which it developed, or one or more component thereof, as an integral part of the tissue. In another embodiment, the tissue equivalent is partially or completely separable from the support on which it developed without causing irreparable damage to the tissue itself. In one embodiment, the tissue equivalent is partially or completely separated from the support.

Any support which facilitates cellular proliferation at the air-liquid interface is suitable for generating the tissue equivalent of the present invention. A variety of such supports are known in the art, and readily adaptable to the present invention by the skilled artisan, inlcueding those discussed in more detail below. In one embodiment, the support on which the tissue develops contains cells which are naturally present in in vivo vaginal tissue (e.g., vaginal fibroblasts or immune cells). When such a support is used, a percentage of the cells which are present in the support are expected to be functionally incorporated into the developing tissue. Depending upon the cell type, some cells may remain in the basal layers, or may migrate further towards the apical layers.

A preferred embodiment of the invention is a cervico-vaginal tissue equivalent which has been generated in serum free medium. Since the contents of serum are not defined and vary between sources and lots, a cervico-vaginal tissue equivalent which is generated in a defined system utilizing serum free medium is a far more reproducible product. Furthermore, the cervico-vaginal tissue equivalent which is generated and maintained in serum free medium may also be far more useful in certain types of assays. For instance, it is more useful for investigating the effect of chemicals which specifically target receptors otherwise activated by components of serum. It is also more useful in investigating the effect of specific chemicals present in serum (e.g., cytokines) which specifically target the tissue. The presence of serum in the generation or maintenance of the tissue may serve to upregulate or downregulate the presence of these targets, or lead to the activation or inactivation of these targets, at best complicating data interpretation, and at worse, leading to the production of inaccurate results. Therefore, in many circumstances, a cervico-vaginal tissue equivalent generated in serum free medium, and optionally maintained in serum free medium, will serve as a far superior model system for the in vivo tissue, compared to a tissue equivalent which is influenced by the presence of serum.

Conditions which enable the generation of the cervico-vaginal tissue equivalent in serum free medium are described below.

II. Generation of the Cervico-Vaginal Tissue Equivalent

Another aspect of the present invention relates to a method of generating the cervico-vaginal tissue equivalent described herein. The methods developed for the production of the cervico-vaginal tissue equivalent are the result of a considerable amount of experimentation.

Generally speaking, the method involves providing vaginal epithelial cells and immune cells of which the final tissue product is to be comprised, and seeding the cells together under conditions appropriate for culture at the air-liquid interface. The seeded cells are then co-cultured at the air-liquid interface under conditions appropriate for differentiation into the cervico-vaginal tissue equivalent described herein.

A. Species and Cell types

The term "vaginal epithelial cells" is intended to include epithelial cells of the vagina and the cervix. The term "immune cells" refers to types of immune cells, or their precursors, found naturally in vaginal or cervical tissue, including Langerhans cells, Langerhans precursor cells (CD34+), monocytes (CD 14+), immature dendritic cells (CD1a+, CD4+), mature dendritic cells (CD86+, HLA-DR++), T cells (CD3+), and macrophages.

The vaginal epithelial cells and immune cells provided for the generation of the tissue equivalent may originate from any number of mammalian species, including mouse, primates, including humans, and animals in artificial breeding programs such as livestock and endangered species. Preferably, the epithelial cells and the immune cells originate from the same species, and preferably the cells used in the generation of the tissue equivalent are of the same species as the model is intended to represent. In a preferred embodiment, the cells are of human origin. The vaginal epithelial cells and immune cells may be generated or derived from a variety of different cell sources.

In one embodiment, the cells are derived directly from in vivo tissue, referred to herein as primary cells. The cells may also be primary cells which have been passaged in culture, referred to herein as passaged primary cells. Passaged primary cells preferably still remain indistinguishable from the initially isolated primary cells, retaining their original characteristics, including growth inhibition, biochemical response, and a finite life span in culture. The skilled artisan will recognize that primary cells derived from malignant tissue may not posses the characteristics of growth inhibition or a finite life span.

Preferably, the tissue from which the primary epithelial cells are derived is ectocervical or endocervical tissue. Both cell types will form stratified, non-keratinized epithelial tissue. The endocervical cells will produce a tissue that is thinner than the tissue produced from ectocervical cells, reflective of the different tissues in vivo.

Primary cells may be obtained from either normal tissue or pathological tissue. A tissue equivalent produced from cells derived from pathological tissue may be particularly useful as a model for vaginal tissue which is in some way pathological. Pathological tissue includes, without limitation, tissue wherein one or more of the cell types present are infected with a pathogen, exhibit reduced growth control in comparison to normal cells, possess an acquired or inherited genetic defect, or are in some other way diseased.

An alternative to the use of primary or passaged primary cells is the use of immortalized or transformed cells. As is known in the art, immortalized cells are characterized as capable of multiple passaging in cell culture without undergoing senescence. Transformed cells share the characteristic of being immortalized, and in addition are not contact inhibited. One of skill in the art will recognize that an immortalized cell is not necessarily a tranformed cell. As known in the art, non-tranformed, non-immortalized cells can undergo only a finite number of passages in cell culture, at the end of which they undergo senescence, which is characterized as a loss of viability, and culminates in complete loss of the ability to propagate the cells in culture. Any combination of primary, passaged primary, transformed and immortalized cells may be used to generate the tissue equivalent.

In another embodiment, the cells provided are originally isolated as primary cells, and then differentiated in culture to a desired phenotype prior to seeding. This approach is particularly useful in generating immune cells for use in producing the tissue equivalent.

Immune cells provided for the generation of the tissue equivalent include Langerhans cells, Langerhans precursor cells (CD34+), monocytes (CD14+), immature dendritic cells (CD1a+, CD4+), mature dendritic cells (CD86+, HLA-DR++), T cells (CD3+), macrophages, or any combination thereof. In addition, any cells which are precursors to these immune cells are also suitable for use, provided they are treated to undergo differentiation into the necessary cell type. Such treatment and differentiation may take place at any point in the generation of the tissue equivalent, for instance, either before seeding, after seeding, or during co-culture. Differentiation of a certain percentage of immune cells may also be an ongoing process throughout the lifetime of the tissue equivalent. Immune cells or precursors thereof, may be isolated from an in vivo source using standard methods known in the art.

In one embodiment, the immune cells provided are generated in vitro from monocytes (CD14+) or from Langerhans precursor cells (CD34+). One such method of generating the immune cells from monocytes is detailed in Example 2, below. Other such methods of generating the immune cells from CD34+ cells are detailed in Example 1 and Example 6, below.

In one embodiment, the method of generating the provided immune cells in vitro from Langerhans precursor cells comprises harvesting CD34+ cells from umbilical cord blood, peripheral blood or bone marrow. The harvested cells are initially cultured in medium comprising about 25 ng/ml stem cell factor, about 200 U/ml GM-CSF, and about 2.5 ng/ml TNF-α, for a time sufficient to produce at least one of the following: an increase in CD1a or HLA-DR expression of the cells, or the presence of Birbeck granules. In one embodiment, the culture period ranges from about 1 to about 10 days, preferably about 7 to about 9 days. Following this culture period, the medium is exchanged for another medium comprising about 25 ng/ml stem cell factor, about 200 U/ml GM-CSF, about 40 ng/ml IL-4, and about 0.5 ng/ml TGF-β1. In one embodiment, this culture period is from about 1 to about 17 days, and preferably is from about 5 to about 10 days, or until the desired amount of immune cells are generated.

In another embodiment, the method of generating the provided immune cells in vitro from Langerhans precursor cells comprises harvesting CD34+ cells from umbilical cord blood, peripheral blood or bone marrow and initially culturing the cells in serum free medium comprising about 20 ng/ml stem cell factor, about 500 U/ml GM-CSF, and about 2.5 ng/ml TNF-α for a time sufficient to produce at least one of the following: an increase in CD1a or HLA-DR expression of the cells, or the presence of Birbeck granules. The period of culture may be at least about 4 days, and may be extended to about 10 days. Culture is then continued in serum free medium comprising about 20 ng/ml stem cell factor, about 500 U/ml GM-CSF, about 2.5 ng/ml TNF-α, about 20 ng/ml Fms-like tyrosine kinase 2 (FLT-3), and about 0.5 ng/ml TGF-β1, for a time sufficient to produce at least one of the following: an increase in CD1a or HLA-DR expression of the cells, or the presence of Birbeck granules. In one embodiment, this is for a period of at least about 5 days. In another embodiment, the period of culture is less than about 20 days. Culture is then continued in serum free medium comprising about 20 ng/ml stem cell factor, about 500 U/ml GM-CSF, about 40 ng/ml IL-4, about 20 ng/ml FLT-3, and about 0.5 ng/ml TGF-β1, for a period of at least about 3 days for a time sufficient to produce at least one of the following: an increase in CD1a or HLA-DR expression of the cells, or the presence of Birbeck granules. In one embodiment, the culture period is less than about 20 days.

In another embodiment, the immune cells are differentiated within the developing tissue equivalent. This can be facilitated by the addition of media supplements which induce or support differentiation of the immune cells, described in detail below.

B. Seeding

The provided vaginal epithelial cells and immune cells are seeded together under conditions appropriate for culture at the air-liquid interface. This involves seeding the cells onto a support which is conducive for growth of the cells at the air-liquid interface. One requirement for the support is that it is porous enough to allow passage of medium from below to the cells. Appropriate supports are discussed in more detail below.

Seeding which is done prior to culture at the air-liquid interface is done by standard methods. This generally involves suspending the desired ratio and quantity of cells in liquid medium and depositing the cell-containing medium onto a support. If the cells are deposited into dish like recepticle which has walls, the bottom of the receptical is the desired support for the culture. Cells settle onto the support. Settling of the cells onto the support after seeding is typically by gravity, and takes anywhere from a few minutes to several hours. One of skill in the art can devise any number of other methods of depositing the cells onto the support, all of which are intended to be encompassed by the present invention. In one embodiment, the amount of cells seeded is about $1 \times 10^3$ to about $1 \times 10^7$ cells/cm$^2$ of vaginal epithelial cells and immune cells. In another embodiment, the amount of cells is about $1 \times 10^5$ to about $1 \times 10^6$ cells/cm$^2$. The ratio of cells seeded is between about 1:1 to 10,000:1 epithelial cells to immune cells. In preferred embodiments, ratios of about 1:1, 10:1, 20:1, or 50:1 epithelial cells to immune cells are seeded.

Supplementing the media with additives which increase immune cell viability and/or cell number permits the seeding of fewer immune cells. Such additives include, without limitation, progesterone (Wieser, F., et al., Fertil Steril., 75, 1234–1235 (2001)), IL-12 (Esche, C., et al., J. Invest. Dermatol., 113, 1028–1032 (1999); Suemoto, Y, et al, J. Dermatol. Sci., 18, 98 108 (1998)), GM-CSF (Caux, C., et al., Nature, 360, 258 (1992)) (Caux, C., et al., Nature, 360, 258 (1992)), and TNF-α (Caux, C., et al., Nature, 360, 258 (1992)). If a variety of different types of immune cells are used, it may be beneficial to increase the overall amount of one or more types of immune cells added to ensure functional incorporation of the desired amount of each type of immune cell.

Once the cells are deposited, the insert is either suspended or supported in the culture dish to allow culture medium to access the underside of the culture, while raising the seeded cells to the air-liquid interface.

If necessary, additional seeding can be performed during culture or co-culture at the air-liquid interface by adding small quantities of medium from above which contains cells to be added onto the culture. When immune cells are added to the culture in this manner, it is advisable to incorporate a chemoattractant, such as GM-CSF, into the medium which the culture is being fed from beneath, in order to stimulate migration of the immune cells into the developing or fully developed tissue.

C. The Support

A preferred receptacle for seeding is a cell culture insert, a variety of which are known and available to the skilled artisan. The skilled artisan can envision additional recepticals, both with and without walls, which will suffice for use in the present method, all of which are intended to be encompassed by the present invention. If the receptical has walls, the walls of the receptacle may consist of polystyrene, polycarbonate, resin, polypropylene, or other biocompatible plastic, with a porous base that serves as a support for the cells to adhere and develop. The porous base or support must allow for passage of media from underneath the developing tissue. The porous base may be a membranous base of polycarbonate or other culture compatible porous membrane such as membranes made of collagen, wettable fluorpolymers, cellulose, glass fiber or nylon attached to the bottom, on which the cells can be cultured. Examples of other suitable supports include, without limitation, an artificial membrane, an extracellular matrix component, a collagen gel, mixture or lattice, in vivo derived connective tissue (preferably derived from vaginal/cervical tissue), a mixed collagen fibroblast lattice, mixed extracellular matrix-fibroblast lattice, plastic, and a collagen sponge (Morota et al., (2000) U.S. Pat. No. 6,051,425). The support porosity must be of sufficient size to allow for passage of media, and can be readily determined by the skilled practitioner. In one embodiment, the porosity is between about 0.2 µm to 10 µm. The porous membrane may also be overlain with one of the other supports described herein.

Preferably, the support components facilitate cellular attachment and development of the tissue. A preferred support is one that contains viable fibroblast cells, such as a mixed collagen fibroblast lattice, a mixed extracellular matrix-fibroblast lattice, or in vivo derived connective tissue (lamina propria). Fibroblasts from a variety of tissue sources can be used (e.g. dermal fibroblasts). Such a support preferably contains fibroblasts which are naturally found in vaginal tissue, referred to herein as vaginal fibroblasts.

The support may also contain additional types of viable cells naturally found in in vivo vaginal tissue, such as immune cells, described herein. In one embodiment, the support contains T cells (CD3+).

D. Culture at the Air-Liquid Interface

Once seeded onto the support, the cells are raised to the air-liquid interface for co-culture under conditions appropriate for differentiation into the cervico-vaginal tissue equivalent described above. For convenience, the term "co-culture," and variations thereof, are used to specify growth and/or differentiation of two or more cell types in direct or indirect contact with one another, at the air-liquid interface. Methods for propagation and differentiation of cells at the air-liquid interface are well known in the art. The co-culture may be incubated, for instance, in a standard tissue-culture incubator under standard conditions. Conditions appropriate for differentiation into the cervico-vaginal tissue equivalent include temperature and content of the atmosphere in which the culture is incubated, media content (discussed in detail below), and optionally, the further seeding of additional cells onto the developing tissue. Preferred temperature and atmospheric conditions are about 37° C. in about 5% $CO_2$, although minor variations may be tolerated.

The period of co-culture at the air-liquid interface can extend from about 1 to about 28 days, although in some instances longer periods may be acceptable. A preferred period of air-liquid interface co-culture is from about 4 to about 11 days.

The amount of medium used can be as little as 0.1 ml per $cm^2$ without any upper limit. Preferably, between 2.0 and 10.0 ml of medium per $cm^2$ is fed to the developing tissue equivalent every other day. Flow through feeding for growth at the air-liquid interface may also be used. Flow through feed rates may be as little as 0.05 ml per $cm^2$ of culture tissue per day. Preferred flow through feed rates are between 1.0 and 5.0 ml per $cm^2$ of cultured tissue per day.

E. Additional Steps

The method for producing the cervico-vaginal tissue equivalent of the present invention may optionally contain additional steps to those described above.

In a preferred embodiment, once the cells are seeded onto the support for growth at the air-liquid interface, they are co-cultivated submerged in growth medium under conditions appropriate for cell propagation, prior to raising to the air-liquid interface for co-culture. The term "co-cultivation," and variants thereof, are used to specify growth and/or differentiation of two or more cell types in direct or indirect contact with one another submerged in media. In one embodiment, this submerged co-cultivation is for a period of about 1 to about 21 days. A preferred submerged co-cultivation period is between 2 and 6 days. Flow through feeding, as described above, may also be used for submerged growth.

At any interim post seeding of the cells provided, onto the porous support, additional cells may be further seeded, either onto the support, or onto the growing/differentiating cells already present on the support, by the methods described above.

In an embodiment of the invention, immune cells and epithelial cells are initially seeded together in a quantity of medium onto the support and allowed to settle. After cell settling and raising of the cells to the air-liquid interface for co-culture, additional immune cells are deposited onto the developing tissue, for continued co-culture and tissue development.

The provided cells may also be manipulated prior to seeding onto the porous support. In one embodiment, the provided cells are additionally cultured submerged in growth medium under conditions appropriate for cell propagation, prior to seeding onto the porous support. During this culture period they may optionally be cultured submerged under conditions appropriate for differentiation. In one embodiment, immune cells, in the form of precursor cells, are first cultured under conditions appropriate for differentiation, prior to seeding.

F. Medium

The medium used for propagation and differentiation of the cells into the tissue equivalent of the present invention influences the properties of the final tissue equivalent product. Unless otherwise stated, the term "medium" as used herein is meant to include both serum containing and serum free medium. "Serum free medium" refers to medium which does not containing serum or a fractionated portion thereof. All components and amounts of serum free medium, in terms of their chemical composition, are defined and relatively pure by tissue culture standards of the art.

The term "differentiation medium" is used herein to refer to medium used for growth of cells at the air-liquid interface. The purpose of this medium is to induce the cells to organize into an in vitro tissue which mimics the in vivo tissue in structure and function. Differentiation medium may also be used to maintain the tissue in a differentiated state for an extended period of time.

A variety of cell culture media known in the art are suitable for use as differentiation medium for co-culture of the epithelial cells and immune cells at the air-liquid interface, the determination of which is within the ability of one of average skill in the art. In one embodiment, the differentiation medium comprises a retinoid, such as retinoic acid, retinol, retinyl acetate, 13-cic retinoic acid, or 9-cis retinoic acid. In a preferred embodiment, the medium comprises about $10^{-5}$ to about $10^{-13}$ M of the retinoid, (e.g., about $5 \times 10^{-10}$ M of a retinoid such as retinoic acid). In one embodiment, the concentration of the retinoid is reduced incrementally over the period of co-culture. For example, the level of retinoic acid may be reduced from about $5 \times 10^{-9}$ M down to about $5 \times 10^{-13}$ M over the course of air-liquid interface culture period.

In a preferred embodiment, the differentiation medium contains one or more of the following supplements: adenine, a-melanocyte stimulating hormone, arachidonic acid, β-fibroblast growth factor, bovine pituitary extract, bovine serum albumin, calcium chloride, calf serum, carnitine, cholera toxin, dibutyl cyclic adenosine monophosphate, endothelin-1, EGF (epidermal growth factor), epinephrine, estradiol, estrogen, ethanolamine, fetal bovine serum, FLT-3 (Fms-like tyrosine kinase 3), glucagon, granulocyte/macrophage-colony stimulating factor, hepatocyte growth factor, horse serum, human serum, hydrocortisone, insulin, insulin-like growth factor 1, insulin-like growth factor 2, interleukin-1β, interleukin-3, interleukin-4, interleukin-6, interleukin-12, interleukin-18, iso-butyl methyl xanthine, isoproterenol, keratinocyte growth factor, linoleic acid, MIP-1α (macrophage inflammatory protein-1α), MIP-3a (macrophage inflammatory protein-3α, newborn calf serum, nor-epinephrine, oleic acid, palmitic acid, phosphoethanolamine, progesterone, stem cell factor, transferrin, transforming growth factor-β1, triiodothyronine, tumor necrosis factor α, vitamin A, vitamin B12, vitamin C, vitamin D, and vitamin E.

In one embodiment, the differentiation medium contains: about a 3:1 ratio of DMEM:Ham's F12, about 10% fetal calf serum, about 10 ng/ml epidermal growth factor, about 0.4 µg/ml hydrocortisone, about $1\times10^{-6}$ M isoproterenol, about 5 ug/ml transferrin, about $2\times10^{-9}$ M triiodothyronine, about $1.8\times10^{-4}$ M adenine, about 5 ug/ml insulin, and about $1\times10^{-6}$ M retinoic acid.

In another embodiment, the differentiation medium is serum free. Serum free medium may be made using basic media or components known in the art (e.g., DMEM (Dulbecco's Modified Eagle's Medium), PRGM (Prostate Epithelial Cell Growth Medium Part # CC-3166, Biowhittaker, Inc.), Ham's F12 medium, MEM (Modified essential medium), McCoy's 5A medium, MCDB 153 (Molecular Cell and Developmental Biology 153 medium) KGM (Keratinocyte growth Medium, Biowhittaker) EpiLife (Cascade Biologics, Inc.), or Medium 199). In one embodiment, the serum free medium is about a 3:1 ratio of DMEM:F12, supplemented with additional defined (non-serum) components, such as retinoic acid, or any of the other defined components described herein.

In a preferred embodiment, the serum free differentiation medium contains about a 3:1 ratio of DMEM:F12, about $5\times10^{-10}$ M retinoic acid, about 0.3 ng/ml keratinocyte growth factor, about 5 ng/ml EGF, about 0.4 µg/ml hydrocortisone, and about 5 µg/ml insulin. In another preferred embodiment, the serum free differentiation medium is DMEM:F12 (about 3:1 ratio) containing retinoic acid (RA) at about $5\times10^{-9}$ M, keratinocyte growth factor (KGF) at about 0.1 nM, about 0.4 µg/ml hydrocortisone, about 5 µg/ml insulin, SCF (about 2.5 ng/ml), GM-CSF (about 20 U/ml), TNF-α (about 0.25 ng/ml), and FLT-3 (about 2 ng/ml).

A variety of cell culture media known in the art is suitable for use as growth medium for co-cultivation of the epithelial cells and immune cells in submerged medium. The term "propagation medium" or "growth medium" is used herein to refer to medium used for growth of the cells in submerged culture. Propagation medium or growth medium, as the terms are used herein, may or may not include supplements which induce or support differentiation of cells in submerged culture, and therefore the use of the term is not restricted to use for cellular propagation absent any level of differentiation of the cells. Examples of such medium include, without limitation, DMEM, PRGM, SFEM (serum free expansion medium), MEM, Medium 199, KGM, EpiLife, MCDB 153, McCoy's 5A.

In one embodiment, the growth medium for co-cultivation of the epithelial cells and immune cells in submerged medium is serum free. One example of serum free growth medium which can be used is (PRGM) containing SCF (about 25 ng/ml), GM-CSF (about 200 U/ml), TNF-α (about 2.5 ng/ml), and FLT-3 (about 20 ng/ml).

The determination of useful concentrations and combinations of the defined medium components or supplements described herein for use as growth medium or differentiation medium are within the ability of one of average skill in the art through no more than routine experimentation, as is the identification of additional supplements or medium components.

III. Use of the Cervico-Vaginal Tissue Equivalent

Another aspect of the present invention relates to methods of use of the cervico-vaginal tissue equivalent. The cervico-vaginal tissue equivalent of the present invention has a variety of different uses in the art. It one respect it serves as a model system for in vivo vaginal and cervical tissue. As such it can be used to determine the possible ill effects of substances used on the in vivo tissue, (e.g., spermicide, medical treatments for infections, and prophylactics for infection).

The MTT assay, described in more detail in the Examples section below, is an assay in which the cervico-vaginal tissue equivalent can be used to predict in vivo ectocervical-vaginal irritation. Other such assays known in the art can be readily used or adapted for use with the cervico-vaginal tissue equivalent. For instance, assays which identify markers of irritation, such as structural damage monitored by histology or the release of pro-inflammatory cytokines, may be used. In addition to irritation, the likelihood of the development of an allergic-type reaction can also be assessed using the tissue equivalent described herein.

Because the cervico-vaginal tissue equivalent is also susceptible to infection by pathogens which infect in vivo vaginal and cervical tissue, it can also be used to determine the efficacy of substances used for treatment or prevention of pathogenic infections. With respect to treatment, it can be used to test the efficacy of substances designed to treat an ongoing infection (e.g., to eliminate the pathogen or prevent further spread of the pathogen). With respect to prevention, it can be used to test the efficacy of microbiocides designed to kill microorganisms in the vaginal canal before they can cause infection, or it can be used to test the efficiency of barrier methods to prevent infection. The tissue equivalent may serve as a model for normal healthy vaginal tissue, or alternatively for pathological vaginal tissue, depending upon the cell types from which it is generated.

As demonstrated in Example 10, the tissue equivalent generated by the methods described herein completely extends across the surface of the tissue culture insert in which it is generated, allowing for topical application of pathogen or treatment or prevention agent without the problem of tissue by-pass. In addition, a large number of highly reproducible tissues can be cultured from a single cervico-vaginal tissue explant.

The ecto-cervical vaginal tissue may also be used in grafting procedures to replace in vivo vaginal or cervical tissue damaged from pathogenic infection, surgery or injury of a compatible individual. Methods of such grafting are generally known or available to the skilled practitioner.

This invention is further illustrated by the following examples which should not be construed as limiting. The contents of all references, patents and published patent applications cited throughout this application, as well as the figures, are incorporated herein by reference.

EXAMPLES

Example 1

Generation and Characterization of the Cervico-Vaginal Tissue Equivalent

A source of both ecto-cervical, endo-cervico, or vaginal epithelial cells along with immune cells such as dendritic, Langerhans, or precursor cells, are necessary to produce the cervico-vaginal tissue equivalent. In this example, primary cervical epithelial cells were obtained from human ecto-cervical tissue. Langerhans cells (CD1a+ cells) were obtained by differentiating Langerhans precursor cells (CD34+ cells) using cytokines. Langerhans precursor cells were harvested from umbilical cord blood samples.

Epithelial Cells

Epithelial cells were obtained from ectocervical tissue and vaginal tissue obtained from women undergoing hysterectomies. After surgical removal of the tissue, the tissue was placed in Dulbecco's Modified Eagle's Medium (DMEM) containing 10× concentrate of penicillin streptomycin (1 mg/ml) and gentamicin (0.5 mg/ml) and stored at 4° C. until the tissue could be processed (within 24 hours). To initiate primary culture, the underlying connective tissue was dissected away from epithelial layers. In certain experiments, the underlying connective tissue was saved in order to harvest vaginal fibroblasts. The epithelial tissue was cut into thin strips, about 1–2 mm in thickness with a scalpel. The strips were then cut numerous times lengthwise to produce small cubes of epithelial tissue. The cubes were about 2 mm×2 mm or smaller. The tissue cubes were then placed in 0.025% trypsin/0.025% EDTA and incubated for 1 hour at 37° C. and 5% $CO_2$. The tissue and trypsin/EDTA mixture was gently stirred occasionally over this time period. After 1 hour, the medium was removed and centrifuged 600× g for 5 minutes to obtain a pellet of ectocervical and vaginal epithelial cells. The medium was aspirated off from the centrifuge tube and the cells were re-suspended in phosphate buffer saline (PBS)/soybean trypsin inhibitor (STI) available from Life Technologies (Rockville, Md.). The cells were then re-centrifuged, the medium removed, and the cells were re-suspended in PRGM, obtained from Biowhittaker, Inc (Walkersville, Md.). The cell/PRGM mixture was then added to tissue culture treated petri dishes for monolayer expansion of the cell number. Between 500 to 5000 cells/$cm^2$ were seeded. The cells were cultured over a 4–10 days period at 37° C. and 5% $CO_2$ until they reached about 70–80% confluency, as observed by low power light microscopy. Trypsin/EDTA was added for 5–9 minutes to detach the cells, as determined by low power light microscopy. The resulting cell suspension was centrifuged, the medium drawn off and discarded, and the cells resuspended in fresh PRGM. The cells were counted and used immediately for seeding of the stratified tissue or, passaged into fresh petri dishes to continue monolayer expansion of the cell number, or cryopreserved for future use. If cryopreserved, the cells were adjusted to approximately $1 \times 10^6$ cells/ml in PRGM/FBS/dimethyl sulfoxide (DMSO), 80/10/10.

Langerhans Cells

Purified CD34+ cells were isolated from umbilical cord blood using immuno-magnetic beads (Dynal Inc., Lake Success, N.Y.). The viability of the cells was checked using the trypan blue exclusion method: viability was >95% for all samples received (n=10). Isolated cells ($2.5 \times 10^5$ cells/ml) were cultured for 11 days in StemSpan™ Serum Free Expansion Medium (SFEM, Stem Cell Technologies, Vancouver, Canada) supplemented with stem cell factor (SCF; 25 ng/ml), granulocyte/macrophage-colony stimulating factor (GM-CSF; 200 U/ml), and tumor necrosis factor (TNF-α; (2.5 ng/ml), and antibiotics. After 4 days, the medium was further supplemented with TGF-β1 (0.5 ng/ml) and culture continued until day 11. Cells were then counted and characterized using FACS for the presence of CD1a, a key surface marker for Langerhans cells. The number of Langerhans precursor cells obtained from 4 representative cord blood samples is shown in Table 1. 40 ml of cord blood yielded an average of $31 \times 10^6$ Langerhans cells, of which 41% were CD1a+, were generated (n=3 preparations). Langerhans precursor cells prepared in this manner were immediately seeded with epithelial cells or cryopreserved at $5 \times 10^5$ cells per ml in freezing medium consisting of StemSpan™ Serum Free Expansion Medium (SFEM, Stem Cell Technologies, Vancouver, Canada) and 10% DMSO.

TABLE 1

Langerhans cells (LC) generated from cord blood derived Langerhans precursor cells (CD34+) using the methods of Example 1

| | LC generated from CD34+ cells from cord blood | | | |
|---|---|---|---|---|
| Donor # | Day 0* | Day 11 | Fold increase | CD1a expression |
| 1 | $0.5 \times 10^6$ | $13 \times 10^6$ | 26 | 33 |
| 2 | $1.6 \times 10^6$ | $32 \times 10^6$ | 20 | 40 |
| 3 | $0.7 \times 10^6$ | $13 \times 10^6$ | 19 | 51 |
| 4 | $1.5 \times 10^5$ | $63 \times 10^6$ | 42 | not measured |

*The first day of culture is designated as Day 0.

Culture of Cells to Produce the Differentiated Tissue $2.5 \times 10^5$ ecto-cervical epithelial cells (EEC) suspended in PRGM and $2.5 \times 10^5$ Langerhans cells suspended in Serum Free Expansion Medium were added to polycarbonate tissue culture treated microporous membrane cell culture inserts available from NalgeneNunc International (Naperville, Ill.). The cell culture inserts were maintained submerged in 1.8 ml of proliferation medium (PRGM) for 3 days in a 37° C. and 5% $CO_2$ incubator. On day 3, the proliferation medium was removed and changed to differentiation medium, consisting of DMEM:F12 (3:1) containing retinoic acid (RA) at $5 \times 10^{-9}$ M, keratinocyte growth factor (KGF) at 0.1 nM, 0.4 μg/ml hydrocortisone, and 5 μg/ml insulin. In contradistinction to the proliferation medium, the differentiation medium was supplied to the basolateral (bottom) surface of the cultures only, through the microporous membrane of the cell culture insert; i.e. the top (apical) surface of the cultures were left dry. This means of culturing the tissue is commonly referred to as culture at the air-liquid interface (ALI). A schematic of the apparatus for growth of the tissue at the air-liquid interface is shown in FIG. 1. Over the next 7 days, the level of RA was reduced from $5 \times 10^{-9}$ M down to $5 \times 10^{-13}$ M. The medium was changed every other day. The tissue generated was characterized as follows.

Histology

Cultures were fixed with 10% formalin, embedded in paraffin and stained with hematoxylin and eosin (H & E). Microtomed cross-sections 3–5 μm thick were observed and photographed using a Nikon Diaphot microscope. Micrographs of typical histological H&E stained cross-sections of the in vitro ectocervical-vaginal tissue were compared to similarly obtained micrographs of normal human ectocervical-vaginal tissue explants.

PAS Staining

The presence of glycogen within the in vitro generated and in vivo cervical-vaginal tissue was determined using the periodic acid Schiff (PAS) reagent. Formalin fixed cross-sections of the in vitro generated and normal human cervical-vaginal tissue were reacted with the PAS reagent and counter stained with hematoxylin using standard histological procedures (Carson, F. I., Histotechnology: A self-instructional text, Amer. Soc. Clin. Pathologist Press, Chicago 112–117 (1997). The two were compared for similarities.

Immunohistochemical Analysis

For cytokeratin analysis of the tissue, 3–5 μm thick paraffin embedded cross-sections were mounted on glass slides and processed for antigen retrieval by heating in a citrate buffer (pH 6.0) for 20 minutes at 95–99° C. After 20 mins, the specimens were removed from the water bath and left standing in the citrate buffer for an additional 20 mins at room temperature (RT). All antibodies were applied at a concentration of 1:30 for 30 minutes at RT. Antibodies specific for CK13 (obtained from Sigma), CK14 (obtained from Research Diagnostics, Inc.), CK16 (obtained from Novacastra), and CK18 (obtained from DAKO, Carpinteria, Calif.), or the dendritic cell marker HLA-DR (mouse anti-human HLA-DR, PharMingen, San Diego, Calif.). A secondary antibody (goat, anti-mouse), was used to identify the primary antibody, and bound antibodies were visualized by means of an alkaline phosphatase detection system using Fast Red (DAKO, Carpinteria, Calif.) as the substrate to stain positive cells red.

Transmission Electron Microscopy (TEM)

Transmission electron microscopy procedures followed those previously described (Cook, J. R., et al. J. Toxicol.: Cutaneous and Ocular Toxic.12: 109–128 (1993)). Briefly, the cultures were fixed at room temperature for 2 hours using 5% glutaraldehyde in 0.1 M sodium cacodylate buffer, pH 7.2. The samples were then rinsed, postfixed in 1% osmium tetroxide in cacodylate buffer, dehydrated in a graded series of ethanols, and embedded in Spurr's low-viscosity epoxy resin (Polysciences, Inc., Warrington, Pa.). Ultrathin sections were mounted on carbon-stabilized Formvar-coated grids and stained with uranyl acetate and lead citrate prior to examination under a Hitachi 7000 transmission electron microscope. TEM facilities at Harvard Medical School (Boston, Mass.) were utilized. TEM micrographs were taken for the in vitro generated cervico-vaginal tissue equivalent and normal human ectocervical-vaginal tissue are shown in. Note, the fixative used for the in vitro generated cervico-vaginal tissue equivalent contained $K_4Fe(CN)_6$, and the fixative used for the excised normal human ectocervical-vaginal tissue did not.

Results

Results of the immunostaining are summarized in Table 2. The in vitro generated cervico-vaginal tissue equivalent exhibited morphology and histology similar to the in vivo tissue. The H&E histological cross-sections indicated that the in vitro generated and in vivo tissue similarly had nucleated basal cells and a number of nucleated suprabasal cell layers. In both tissues examined, these layers were followed by layers in which nuclei and organelles were lost and cells became filled with glycogen, as seen in the photo-micrographs of PAS reacted cross-sections of the in vivo and in vitro tissue. In both tissues, the intensity of glycogen staining increased as the apical surface was approached.

When glycogen content was assayed, it was seen that the cells of both the in vitro generated and normal human ectocervical-vaginal tissue similarly became progressively filled with glycogen and lost their organelles towards the apical surface.

The in vitro generated cervico-vaginal tissue equivalent was analyzed for the presence of cellular markers found in vivo, by immunohistochemical analysis. The presence of cytokeratins detected in the in vitro and in vivo tissues is summarized in Table 2. CK14 was observed in the basal layers, and CK13 was observed in the more differentiated suprabasal layers of both the in vitro generated and excised normal human ectocervical tissue. No expression of CK18 was observed in either tissue.

TABLE 2

Cytokeratin expression of in vitro generated cervico-vaginal tissue equivalent and in vivo ectocervical tissue

| Cytokeratin | In vitro tissue | In vivo tissue | Antibody source | Notes |
| --- | --- | --- | --- | --- |
| CK13 | Suprabasal | Suprabasal | Sigma | Observed in Fichorova, R. N., et al., Biol. of Reproduction, 57, 847–855 (1997) |

TABLE 2-continued

Cytokeratin expression of in vitro generated cervico-vaginal tissue equivalent and in vivo ectocervical tissue

| Cytokeratin | In vitro tissue | In vivo tissue | Antibody source | Notes |
| --- | --- | --- | --- | --- |
| CK14 | Dark basal staining | Light basal staining | Research Diag. Inc. | Basal cell marker (Rajan, N., et al., J. of Urol., 163, 616–622 (2000)) |
| CK16 | Light Suprabasal | None | Novocastra | Light staining in Fichorova, R. N., et al., Biol. of Reproduction, 57, 847–855 (1997) |
| CK18 | No staining | No staining | DAKO | Same result as Fichorova, R. N., et al., Biol. of Reproduction, 57, 847–855 (1997) |

The in vitro generated cervico-vaginal tissue equivalent was also characterized for the presence of Langerhans cells by staining for the presence of the Langerhans cell marker HLA-DR. Langerhans cells expressing HLA-DR were observed in the in vitro generated tissue in similar location and density to those seen in the excised normal human ectocervical-vaginal tissues. The HLA-DR positive cells were present in the suprabasal layers of the tissue equivalent, similar to the in vivo tissue. This indicates that the in vitro generated tissue had incorporated the Langerhans cells similarly to the normal human tissue. The in vitro generated cervico-vaginal tissue equivalent was further characterized morphologically by transmission electron microscopy. This analysis revealed morphological features characteristic of normal ectocervico vaginal epithelium (Sargeant, P., et al.,J. Submicrosc. Cytol. Pathol., 28, 161–170 (1996)), in that the cells nearing the apical surface of the in vitro generated tissue became highly interdigitated in a zipper-like pattern. In addition, microridges on the apical surface were apparent. Numerous desmosomes were also observed between the cells located in the lower layers of the tissue.

Example 2

Use of Langerhans Cells Derived from Monocytes to Generate the Cervico-Vaginal Tissue Equivalent Langerhans cells isolated from monocytes performed equally well in the generation of the in vitro ectocervico-vaginal tissue. Experiments identical to those performed in Example 1 were performed on in vitro generated cervico-vaginal tissue equivalent which contained Langerhans cells generated from monocytes.

Generation of Langerhans Cells from Precursor Cells

Purified macrophages were negatively isolated from cord blood/adult blood derived mononuclear cells (MNC) with immuno-magnetic beads (Dynal Inc., Lake Success, N.Y.) following the manufacturer's recommendation, or by plastic adhesion. MNC ($1 \times 10^7$) were re-suspended in 200 $\mu$l PBS supplemented with 0.1% bovine serum albumin (BSA), 20 $\mu$l of blocking reagent, and 20 $\mu$l antibody mix (monocyte-kit provided by Dynal) and incubated at 4° C. for 10 min. Cells were then washed 2× and re-suspended in PBS containing 0.1% BSA. Depletion Dynalbeads (100 $\mu$l/$1 \times 10^7$ cells) were then added and cells were incubated at 4° C. for 15 min with gentle tilting and rotation. The cells were pipetted up and down and then magnetic separation of the bead-cell rosettes was performed using Dynal Magnetic Particle Concentrator (MCP)-6 for 2 min. The supernatant containing the negatively isolated macrophages was collected and centrifuged. Isolated macrophages were then counted, cultured or cryopreserved in liquid $N_2$ until use. Isolated monocytes ($5.0 \times 10^5$ cells/ml) were cultured for 8 days in OPTI-MEM medium (GIBCO BRL Life Technologies, Rockville, Md.) supplemented with GM-CSF (200 U/ml), IL-4 (200 U/ml), 5% fetal bovine serum (FBS), and antibiotics. After 8 days of culture, Langerhans cells were produced from the culture.

Langerhans cells were combined with ectocervicovaginal cells and cultured as described in Example 1 to produce the differentiated tissue. The tissue generated was assessed by the same means as in Example 1, which produced identical results.

Example 3

Use of Langerhans Precursor Cells

This example is identical to Example 1 except that Langerhans precursor cells were used instead of Langerhans cells. Cytokines were added to the proliferation and differentiation medium to allow maturation of the Langerhans precursor cells into Langerhans cells, in situ as the tissue developed.

$2.5 \times 10^5$ ecto-cervical epithelial cells (EEC) suspended in PRGM and $2.5 \times 10^5$ Langerhans precursor cells suspended in SFEM were added to polycarbonate tissue culture treated microporous membrane cell culture inserts obtained from NalgeneNunc International (Naperville, Ill.). The cell culture inserts were maintained submerged in 1.8 ml of proliferation medium (PRGM) containing SCF (25 ng/ml), GM-CSF (200 U/ml), TNF-α (2.5 ng/ml), and FLT-3 (20 ng/ml) for 7 days in a 37° C. and 5% $CO_2$ incubator. On day 7, the proliferation medium was removed and changed to differentiation medium, consisting of DMEM:F12 (3:1) containing retinoic acid (RA) at $5 \times 10^{-9}$ M, keratinocyte growth factor (KGF) at 0.1 nM, 0.4 µg/ml hydrocortisone, 5 µg/ml insulin, SCF (2.5 ng/ml), GM-CSF (20 U/ml), TNF-α (0.25 ng/ml), and FLT-3 (2 ng/ml). In contradistinction to the proliferation medium, the differentiation medium was supplied to the basolateral (bottom) surface of the cultures only, through the microporous membrane of the cell culture insert; i.e. the top (apical) surface of the cultures were left dry. As per Example 1, over the next 7 days, the level of retinoic acid was reduced from $5 \times 10^{-9}$ M down to $5 \times 10^{-13}$ M. The medium was changed every other day.

This produced a tissue equivalent similar to that produced with Langerhans cells in Examples 1 and 2, as analyzed by the methods described therein.

Example 4

Addition of Collagen Gel/Fibroblast Matrix

This example is identical to Example 1 except that a collagen gel/fibroblast matrix was prepared on the polycarbonate tissue culture microporous membrane cell culture inserts prior to addition of the epithelial and Langerhans cells. Fibroblasts were harvested from the underlying connective tissue which was dissected away from the ectocervical epithelial tissue of Example 1. Similar to the epithelial tissue, it was cut into thin strips, about 1–2 mm in thickness with a scalpel. The strips were next cut numerous times lengthwise so that the result was small cubes of connective tissue. Preferably the cubes were about 2 mm×2 mm or smaller. The tissue cubes were then placed into a 100-mm tissue culture treated petri dish with 2–3 drops of DMEM+ 10% FCS+antibiotics (0.25 µg/ml fungizone, 0.5 mg/ml gentamicin, and 1 mg/ml penicillin/streptomycin) on each cube. The petri dish was next placed in the incubator for 3 days at 37° C. and 5% $CO_2$. After 3 days, any unattached pieces of tissue were removed with a sterile forceps and 10.0 ml of DMEM+10% FCS+antibiotics were added. Cultures were returned to the incubator, fed every other day with 10.0 ml of DMEM+10% FCS+antibiotics for 27 days. On day 27 when the cells became 90–95% confluent, as observed by low power light microscopy, the medium was removed and the petri dish was washed with 10 ml PBS. Next, the cells were detached from the petri dishes by treating with 2.0 ml of 0.025% trypsin/0.025% EDTA for approximately 30 minutes (detachment of cells from the petri dish was followed using low power 4× objective microscopic examination). Trypsin/EDTA was removed and 2 aliquots of 10 ml of soybean trypsin inhibitor (STI), obtained from Life Technologies (Rockville, Md.), were added. The STI cell mixture was then centrifuged 600× g for 5 minutes to obtain a pellet of vaginal fibroblast cells. The medium was aspirated off from the centrifuge tube, the cells were re-suspended in DMEM/10% FCS+antibiotics available from Biowhittaker, Inc (Walkersville, Md.) and the cells were counted. Using this method, $4.5 \times 10^6$ fibroblasts were obtained from a single surgical explant. The fibroblasts were used immediately to form the collagen gel/fibroblast matrix, described below, or cryopreserved for future use. If cryopreserved, the cells were adjusted to $1 \times 10^6$ cells/ml in DMEM/FCS/dimethyl sulfoxide (DMSO), 80/10/10.

The collagen gel-fibroblast matrix was prepared by mixing 6.4 ml of type 1 rat-tail collagen (5.0 mg/ml) with 1.6 ml of 0.1% acetic acid, 1 ml of chilled 10× Hanks Buffered Saline solution (HBSS) supplemented with phenol red (pH 7.2); this solution was adjusted to neutral pH. Next, 1 ml of Fetal Calf Serum (FCS) containing $6 \times 10^5$ vaginal fibroblasts were added to the collagen-fibroblast solution. 250 µl of this mixture were added to culture inserts and allowed to gel by incubating inserts at 37° C. for 1 hr. The collagen gel/ fibroblast/matrix was then equilibrated with PRGM medium by submerging the inserts in 2 ml of medium, followed by incubation at 37° C. for 48 hr. Next, appropriate amounts of the epithelial and dendritic cell suspensions were added onto the apical side of the cell culture inserts which was covered with the collagen gel/fibroblast matrix. Culture conditions were continued as per Example 1. The same method can be employed using the Langerhans cells of Example 2 or the method of Example 3, using Langerhans precursor cells.

An H&E stained histological cross-section of the tissue produced using the collagen gel-fibroblast matrix produced tissue which looked identical to the tissue produced in Example 1.

Example 5

Addition of T-Cells to Collagen Gel/Fibroblast Matrix

The procedures followed in this example were identical to those of Example 4 except that T-cell enriched peripheral blood mononuclear cells (PBMC) were added to the collagen gel/fibroblast matrix. PBMC were separated from cord blood cells using a Histopaque gradient (Sigma Chemical Company, St. Louis, Mo.). 40 ml of cord blood yielded an average of $1 \times 10^8$ PBMC using this method. Approximately $1 \times 10^7$ PBMC were re-suspended in 200 µl PBS supplemented with 0.1% bovine serum albumin (BSA), 10% fetal calf serum, and 20 µl antibody mix (T-cell negative isolation kit provided by Dynal, Inc., Lake Success, N.Y.) and incubated at 4° C. for 10 min. Cells were then washed 2× and re-suspended in PBS containing 0.1% BSA. Depletion Dynal beads (100 µl/1×10⁷ PBMC) were then added and cells were incubated at room temperature for 15 min with gentle tilting and rotation. The cells were pipetted up and down and then magnetic separation of the bead-cell rosettes was performed using Dynal Magnetic Particle Concentrator (MCP)-6 for 2 min. The supernatant containing the negatively isolated T cells was collected and centrifuged. The isolated T cells were then counted. An average of 25×10⁶ T cells were isolated from 40 ml of cord blood. The viability of these cells was >95%, as determined by trypan blue exclusion, and phenotypic characterization of these cells showed a high expression of CD3 (>70%), the T cell marker. 25,000 T cells were added to 250 µL of the collagen/vaginal fibroblast mixture of Example 4 which was added to the cell culture inserts.

Next, appropriate amounts of the epithelial and dendritic cell suspensions were added onto the apical side of the cell culture inserts which was covered with the collagen gel/fibroblast matrix. Culture conditions were continued as per Example 1. The dendritic cells of Example 2 and/or the Langerhans precursor cells of Example 3 can also be incorporated into the collagen gel/fibroblast matrix by an adaptation of these methods.

The histology of the resulting tissues was identical to that of the tissue of Example 4. Immuno-staining of tissue cross-sections identified incorporated, viable T cells in the underlying collagen matrix of the differentiated tissue. The T-cells stained positive with a monoclonal antibody for CD3 (T-cell marker). In control tissues to which T-cells were not added to the collagen matrix, no staining was observed.

Example 6

Use of Passaged Epithelial Cells and an Improved Method of Preparation of Langerhans Cells Primary epithelial cells harvested from ectocervical tissue as described in Example 1 were cryopreserved at 1×10⁶ cells/ml in PRGM/FBS/dimethyl sulfoxide (DMSO) in 0.5 ml cryovials. The contents of the cryovial were thawed in a 37° C. water bath and added into two 150 mm diameter tissue culture treated petri dish containing 30 ml of PRGM. The epithelial cells were fed every other day until day 7 at which point they were 70–75% confluent. The cells were detached from the petri dishes by treating with 5.0 ml of 0.025% trypsin/0.025% EDTA for approximately 1 minute (detachment of cells from the petri dish was followed using low power 4× objective microscopic examination). Once the cells detached, the excess trypsin was neutralized with Soybean Trypsin Inhibitor (STI) and the cells were suspended and triturated in PRGM medium. These second passage cells were added to the cell culture inserts in the same way as the primary epithelial cells used in Example 1.

Purified CD34+ cells were isolated from umbilical cord blood using immuno-magnetic beads (Dynal Inc., Lake Success, N.Y.). The viability of the cells was checked using the trypan blue exclusion method: viability was >95% for all samples received (n=10). Isolated cells (2.5×10⁵ cells/ml) were cultured for 3 days in serum free growth medium supplemented with stem cell factor (SCF; 20 ng/ml), granulocyte/macrophage-colony stimulating factor (GM-CSF; 500 U/ml), and tumor necrosis factor (TNF-α; 2.5 ng/ml), and antibiotics. On Day 4, the medium was further supplemented with 0.5 ng/ml TGF-β1 and 20 ng/ml FLT-3 and the culture was continued until day 9. On day 9, the TNF-α was removed and 40 ng/ml of IL-4 was added. On Day 12, the cells were counted and characterized using FACS for the presence of CD1a, a key surface for Langerhans cells The number of Langerhans cells and the CD1a expression for Langerhans cells obtained from 5 representative cord blood samples are shown in Table 3. 40 ml of cord blood yielded an average of 128×10⁶ Langerhans cells (n=5 preparations), of which 53% were CD1a+, were generated (n=3 preparations). Langerhans cells prepared in this manner were either immediately seeded with epithelial cells, or cryopreserved at 5×10⁵ cells per ml in freezing medium consisting of StemSpan™ Serum Free Expansion Medium (SFEM, Stem Cell Technologies, Vancouver, Canada) and 10% DMSO, for future use.

A differentiated tissue was produced using these cells and the methods described in Example 1. Cells were maintained submerged for 5 days and grown at the air-liquid interface for 7 days. IL-12 (1 ng/ml) and retinoic acid ($5 \times 10^{-10}$ M) were added to the differentiation medium described in Example 1. These concentrations were maintained throughout the culture period. All other conditions were the same as described in Example 1. An H&E stained cross-section of ectocervical/Langerhans cell tissue comprised of second passage cells was identical to the tissue produced in Example 1.

TABLE 3

LC generated from cord blood derived adherent monocytes using methods of Example 6

LC generated from CD34 + cells from cord blood

| Donor # | Day 0* | Day 11 | Fold increase | CD1a expression |
|---|---|---|---|---|
| 212 | 1.4 × 10⁶ | 176 × 10⁶ | 126 | n.m. |
| 264 | 1.36 × 10⁶ | 134 × 10⁶ | 99 | 54% |
| 269 | 0.72 × 10⁶ | 60 × 10⁶ | 83 | 45% |
| 277 | 1.9 × 10⁶ | 148 × 10⁶ | 78 | 59% |
| 285 | 1.8 × 10⁶ | 121 × 10⁶ | 67 | n.m. |

*The first day of culture is designated as Day 0.
n.m. = not measured

Example 7

Serum Free Growth Medium to Produce Langerhans Cell/Cervico-Vaginal Tissue Equivalent Cryopreserved, skin-derived, normal human epidermal keratinocytes (NHEK) were purchased from Cascade Biologics (Portland, Oreg.) and proliferated in monolayer culture in Medium 154 supplemented with Human Keratinocyte Growth Supplement (Cascade Biologics) as per instructions provided by the Cascade Biologics. Ectocervical epithelial cells (EEC) were isolated from ecto-cervical tissue as described in Example 1. In addition, Langerhans cells were prepared as described in Example 1. Nunc cell culture inserts were then seeded with 125,000 Langerhans cells and 250,000 of either a) normal human epidermal keratinocytes or b) ecto-cervical epithelial cells. These tissues were maintained in 2.0 ml of PRGM for 4 days submerged with medium changes every other day. On day 4, the tissues were raised to the Air-liquid interface and an additional 125,000 Langerhans cells were seeded into the inserts. At the air liquid interface, 5.0 ml of the following medium was used: DMEM:F12 (3:1)+$5 \times 10^{-10}$ M RA, 0.3 ng/ml KGF, 5 ng/ml EGF, 0.4 µg/ml hydrocortisone, and 5 µg/ml insulin.

H&E histological cross-sections of in vitro generated cervico-vaginal tissue produced and in vivo cervico-vaginal tissue were analyzed and compared to an H&E histological cross-section of tissue produced when epidermal keratinocytes are grown using the same culture medium. The ectocervico-vaginal cells produced tissue which was very similar to the in vivo tissue. On the other hand, the tissue produced from the epidermal keratinocytes was very similar to skin as evidenced by the presence of a granular layer and stratum corneum. Other features of the in vitro generated cervico-vaginal tissue were equivalent to those discussed above.

Example 8

Use of Serum Containing Medium

This example is similar to Example 1, except that the medium used to differentiate the tissue was a 3:1 ratio of DMEM:Ham's F12, 10% fetal calf serum, 10 ng/ml epidermal growth factor, 0.4 µg/ml hydrocortisone, $1 \times 10^{-6}$ M isoproterenol, 5 ug/ml transferrin, $2 \times 10^{-9}$ M triiodothyronine, $1.8 \times 10^{-4}$ M adenine, 5 ug/ml insulin, and $1 \times 10^{-6}$ M retinoic acid. The culture was maintained for 5 days in submerged culture using 2.0 ml of this medium, with medium changes every other day. The culture was then placed at the air liquid interface, using 5.0 ml of the same medium except the isoproterenol, transferrin, triiodothyronine, and adenine were removed. Tissue, whose histology was equivalent to that of the tissues generated in the examples above (within the normal minor fluctuations observed in these types of cultures), was obtained. Other features of the tissue equivalent to those of the above described tissues were also observed.

Example 9

Use of Tissue Model to Predict Vaginal Irritation

The ectocervico-vaginal tissue culture generated above, in Example 1 was used to correlate in vivo irritation results using the MTT assay.

MTT Tissue Viability Assay

Figure 2:
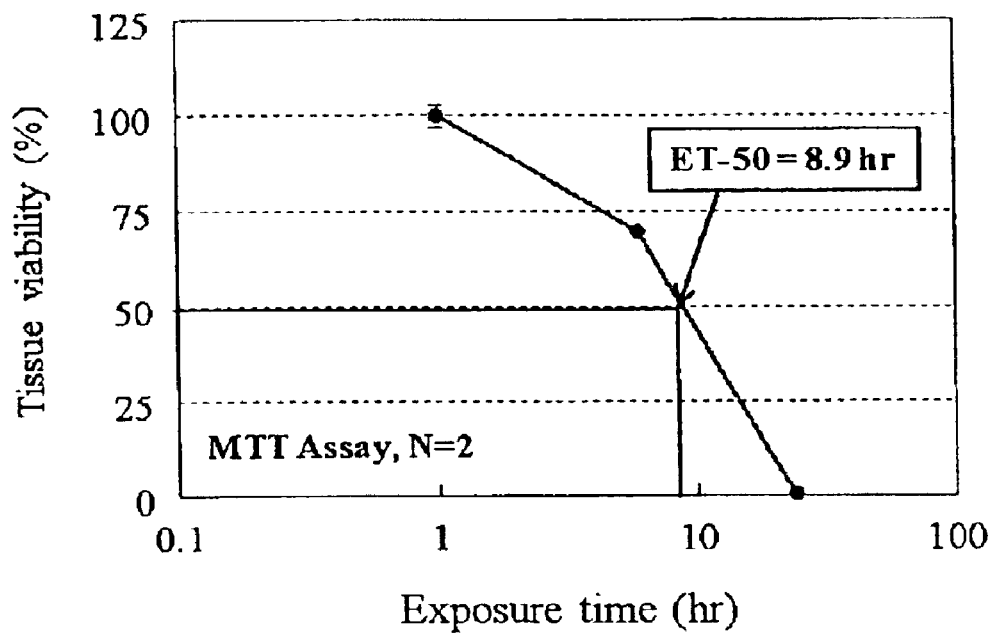
FIG. 2 is a dose response curve plotting tissue viability of the in vitro generated cervico-vaginal tissue against exposure time to the commercial spermicide nonoxynol-9 (2%). The graphical determination of the exposure time required to reduce tissue viability to 50% (ET-50) is illustrated.

The MTT tissue assay provides a facile, accurate means of quantifying the overall viability (Mosmann, T., J. Immunol. Meth., 65, 55 (1983)) and reproducibility (Klausner, M., Kubilus, J., et al., in *Advances in Animal Alternatives*, eds. Salem, H., Katz, S. A., Taylor & Francis, Washington, D.C., 347–357 (1997)). MTT (3-(4,5-dimethylthiazole-2 yl)-2,5-diphenyl tetrazolium bromide) is a dye which is taken up by viable cells and reduced by mitochondrial dehydrogenases to form a purple formazan. Only viable cells with functioning mitochondria will perform this reaction, therefore the amount of colored formazan produced is proportional to the number of viable cells (Mosmann, T., J. Immunol. Meth., 65, 55 (1983)). In the assay, tissue cultures are exposed to a test material, which is applied to the apical surface of the cultures for various time periods. Cellular damage caused by the test material is quantitated by subjecting the exposed tissue to the MTT assay, and comparing the results to unexposed tissue similarly assayed. A sample dose response curve for the in vitro generated cervico-vaginal tissue equivalent exposed to the common spermicide, Nonoxynol-9 is shown in FIG. 2. The graphical determination of the exposure time required to reduce tissue viability to 50% (ET-50) is illustrated. Actual calculation of ET-50 is done using mathematical interpolation. More irritating materials have shorter ET-50's; less irritating materials have longer ET-50's, or will cause less than 50% reduction in tissue viability even for very long exposure times. This assay is commonly used to predict dermal irritation (Perkins, M.A., Osborne, R., Rana, F. R., Ghassemi, A., and Robinson, M. K., "Comparison Of In Vitro And In Vivo Human Skin Responses To Consumer Products And Ingredients With A Range Of Irritancy Potential," *Toxicological Sciences*, 48, 218–229 (1999); Genno, M., Yamamoto, R., Kojima, H., Konishi, H. and Klausner, M., "Evaluation of a New Alternative to Primary Draize Skin Irritation Testing Using The EpiDerm™ Skin Model," *Altern. Animal Test. Experiment.* 5, 195–200 (1998)) and ocular irritation, using the non-cornified epithelial tissue model, EpiOcular™ (Stern, M., et al, Toxicology In vitro, 12, 455–461, (1998)).

Use of the Cervico-Vaginal Tissue Equivalent in the MTT Assay

The in vitro generated cervico-vaginal tissue equivalent, produced as described in Example 1, and the EpiOcular™ ocular tissue (Stern, M., et al, Toxicology In vitro, 12, 455–461, (1998)), were exposed to 100 mg of three test materials: 1) KY Brand Jelly personal lubricant (Personal Products Company, Division of McNeil-PPC, Inc., Skillman, N.J., 08558); 2) KY Plus 2% Nonoxynol-9 Lubricant Spermicide (Personal Products, Company); and 3) an experimental formulation of KY Plus 12% Nonoxynol-9, prepared by adding 10% of Nonoxynol-9 (JEECHEN NP-9, JEEN International Corporation, Fairfield, N.J.) to the commercially available KY Plus Nonoxynol-9 (2%) Lubricant Spermicide. Each of these products was exposed to duplicate tissues for 1–24 hours. Due to the high viscosity, gel-like nature of the KY Jelly, 100 mg of the formulation was spread evenly over a flat end of an applicator pin with a circular area of 0.50 cm². The applicator pin was then inverted and placed gently in contact with the apical surface of the tissue. The applicator pin was left in place for the duration of the exposure, during which the tissue was incubated at 37° C. and 5% $CO_2$. After each exposure time was complete, the test material was rinsed off the tissue by submerging the tissue culture insert, at least 3 times, in a beaker containing PBS and then decanting. Additional PBS rinse/decant cycles were performed if there was any evidence that the test material had not been completely removed. After rinsing, the tissue was submerged in 5.0 ml of assay media in a 12-well plate for 10 minutes to insure complete removal of the test material.

After the allotted exposure time, and rinsing of the test material from the tissue, the cultures were "loaded" with 1 mg/ml of MTT dye in culture medium. The purple formazan dye was then extracted overnight using 2.0 ml of isopropyl alcohol and the formazan extract quantified by measuring optical density (OD) at 570 nm in an E-MAX 96-well plate reader (Molecular Devices, Menlo Park, Calif.).

The viability of the tissue was normalized as a percent of unexposed control tissues which were also loaded with MTT and extracted in an identical manner. The % of viable cells remaining was determined using the equation: % viability= OD (treated tissue)/OD (control tissue). A dose response curve was constructed by plotting the percent viability versus the time of exposure to the surfactant solution. The exposure time required to reduce the viability to 50% (ET-50) was determined mathematically.

Results

The MTT assay was performed for KY jelly and KY jelley containing various N-9 concentrations, using the in vitro generated cervico-vaginal tissue equivalent generated in Example 1, and also the non-cornified epithelial tissue model, EpiOcular™. The determined ET-50's for the various test materials are shown in Table 4.

TABLE 4

ET-50 for 3 spermicide products containing Nonoxynol-9 (N9) tested in EpiOcular (OCL-200) and in vitro generated cervico-vaginal tissue equivalent

| Product/Formulation | OCL-200 ET-50 (hr) | Ocular Irritation | ECV ET-50 (hr) |
|---|---|---|---|
| KY Brand Jelly | 22.1 | Non-irritating | >24 |
| KY + N9 (2%) | 2.1 | Minimal | 8.9 |
| KY + N9 (12%) | 0.62 | Mild | 6.5 |

The in vitro generated cervico-vaginal tissue equivalent and ocular tissues were shown to have significantly different susceptibilities to KY jelly and various N-9 concentrations tested. As expected, lower ET-50's were obtained for higher N-9 concentrations, i.e. higher N-9 concentrations caused more tissue cytotoxicity and were thereby predicted to be more irritating. In fact, although N-9 is the most commonly used spermicidal contraceptive used in the U.S. (D'Cruz, O. J., et al, AAPS PharmSciTech, 2(1), article 6 (2001)), N-9 has been shown to cause ectocervical-vaginal irritation in the finite segment of the population (Reckart, M. L., J. AIDS, 5, 425–427 (1992)). In one study which evaluated the use of N-9 as an HIV microbicide, 25% of volunteers experienced ectocervical-vaginal irritation (Stafford, M K., et al., J Acquir Immune Defic Syndr Hum Retrovirol., 17, 327–331 (1998)).

Example 10

HIV Virus Does Not Pass Through Ectocervical-Vaginal Tissue Equivalent

The in vitro generated cervico-vaginal tissue equivalent of the present invention can be used to study the mechanisms of HIV infection and transmission and provides an in vivo-like means of testing microbicides or other prophylactic means of preventing virus transmission. One unanswered question regarding infection and transmission of HIV is whether or not HIV can permeate the ectocervical or vaginal tissue. In this example, the cervico-vaginal tissue equivalent was used to determine the ability of HIV virion to pass through the ectocervico-vaginal tissue.

Virus Stock

HIV-1 virus stocks were produced by transfecting 293T cells with 15 μg of either pNL4-3 (plasmid for T-cell tropic virus, NL4-3) or pAD8 (plasmid for macrophage tropic virus, ADA) plasmid DNAs. At 12 hrs following transfection, cells were washed and cultured in RPMI supplemented with 10% fetal calf serum (FCS) and antibiotics. After 24 hr, culture supernatants containing full-length virus were harvested and filtered using 0.45 μm pore size filters and analyzed by using reverse transcriptase (RT) assay.

Reverse Transcriptase (RT) Assay for HIV

A reverse transcriptase (RT) assay was used to determine the relative amount of HIV present in supernatants following HIV permeation and infection experiments. One ml of supernatant was collected and centrifuged at 12,000 rpm for 30 minutes. The supernatant was discarded and the virus pellet was re-suspended in 10 μl of RT suspension buffer containing 50 mM Tris buffer-HCl pH 7.5, 1 mM dithiothreitol (DTT), 20% glycerol, 0.25 M KCL, and 0.25% triton X-100. Three freeze/thaw cycles (37° C./−78° C.) were used to lyse any virus in the supernatants. Next, 40 μl of RT assay mixture containing RT assay buffer (250 mM Tris Buffer, pH 7.5, 37.5 mM $MgCl_2$, and 0.25% triton X-100), and DTT, Oligo-dT-poly (A), [$^3$H] dTTP was added to the virus lysate. The samples were vortexed and incubated at 37° C. for 1 hr. In this assay, the Oligo(dT-15) served as a primer for the incorporation of [$^3$H] dTTP by RT on a poly(A) template (Boeringer Mannheim, Indianapolis, Ind.). The labeled reaction product was then allowed to bind on a nitrocellulose membrane and washed by submerging 3 times (10 min/wash) in 2× SSC buffer (Sigma Chemical Co.). The membranes were further washed 2× with 95% ethanol (10 seconds/wash) and allowed to dry using a heating lamp. Quantitative results of relative virus levels were obtained using a scintillation counter.

Passage of HIV Through the Tissue

Virus was topically applied to the cerivco-vaginal tissue equivalent or directly to the underlying 0.4 μm microporous membrane (upon which the tissue is cultured). The tissue culture inserts with or without the cervico-vaginal tissue equivalent were placed in 6-well plates along with 2.0 ml of culture medium and the 108 μL of ADA virus (50,000 CPM, as measured in the RT assay) was topically applied. The medium beneath the inserts was assayed at 2, 5, and 24 hours after virus application. After 24 hours, the apical surface of the inserts was washed and the bare and tissue-containing inserts were returned to the incubator for an additional 48 hours (72 hour total). The medium samples were assayed for HIV using the RT assay. Results are shown in Table 5.

Results

Results of the analysis are summarized in Table 5.

TABLE 5

Accumulation of NL4-3 virus in medium beneath: A) tissue culture membrane alone or B) Ectocervical tissue grown atop the membrane. At time 0, virus was applied topically (50,000 CPM). Aliquots of medium beneath tissue culture inserts were collected at times indicated and analyzed for virus passage through the tissue using a reverse transcriptase assay.

| | A. Membrane only | | B. Membrane + ecto-cervical tissue | |
|---|---|---|---|---|
| Time (hr) | Cumulative amount of virus in medium (CPM) | % of virus applied | Cumulative amount of virus in medium (CPM) | % of virus applied |
| 2 | 22265 | 44.5 | 25 | 0.1 |
| 5 | 28586 | 57.2 | 25 | 0.1 |
| 24 | 28586 | 57.2 | 208 | 0.4 |
| 72 | 30072 | 60.1 | 195 | 0.5 |

Comparison of the results obtained with the bare insert and with the cervico-vaginal tissue equivalent (Table 4) indicated that the HIV virion cannot permeate through the ectocervical-vaginal tissue. Within 2 hours, 44% of the virus had passed through the 0.4 um membrane of the bare cell culture inserts. After 5 hours, the vast majority of the virus (57% of 60.1%) which would pass through the tissue had already done so. No virus was detected passing through the cervico-vaginal tissue equivalent over the 72-hour period studied. Over the entire 72-hour experiment, 60% of the applied virus was recovered in the medium beneath the bare inserts. The remaining 40% had likely degraded (See Table 6). However, no virus was detected in the culture medium which had passed through the cervico-vaginal tissue equivalent (Note: The low values in Table 5 are baseline readings for the RT assay—i.e. no virus can be detected which has passed through the tissue).

Example 11

HIV Virus Infects the Cervico-Vaginal Tissue Equivalent

The ability to monitor HIV infection and transmission was monitored in the in vitro generated cervico-vaginal tissue equivalent utilizing the reverse transcriptase assay described in Example 10, and the Polymerase Chain Reaction (PCR), to detect HIV transcripts within the DNA of the cervico-vaginal tissue equivalent.

Polymerase Chain Reaction (PCR) for HIV Transcripts

In the preparation of DNA lysates for PCR analysis, tissue samples were washed twice with PBS by centrifugation. Cellular DNA extraction was then performed using Qiagen DNeasy™ Tissue Kit (Qiagen Inc., Valencia Inc, CA) using the manufacturer's protocol. In this assay, tissue samples were lysed by the addition of Proteinase K (15 μl/tissue) and incubation at 55° C. for 1 hr followed by 10 min incubation at 70° C. The lysate was then loaded onto a DNeasy™ mini membrane column. The DNA was selectively bound to this membrane, therefor contaminants were removed with two washes. DNA was then eluted by adding 50 μl elution buffer (two times). DNA was quantified by spectrophotometer (the 260/280 absorbance ratio ranges from 1.81 to 1.97). Total DNA (0.6 μg) was examined for HIV DNA by polymerase chain reaction (PCR).

Primers specific for the gag gene of ADA were designed using Primer 3 genome software provided by the Whitehead Institute (Massachusetts Institute of Technology, Cambridge, Mass.) on the world wide web. Primer sets were: forward primer, 5'CAGCAT GTCAGGGAGTAGGG-3' (SEQ ID NO: 1); and reverse primer, 5' TTGTCTATCG-GCT CCTGCTT-3 (SEQ ID NO: 2) and obtained from the Great American Gene Company (Ramona, Calif.).

DNA-PCR was performed by adding gene specific primers with a final primer concentration of 0.4 μM each, total DNA (600 ng), 1.0 unit of Taq polymerase, buffer (5 μl), 200 mM of each dNTPs, and dH2O (to make a final volume of 50 μl). The samples were run on a thermocycler (Perkin Elmer Cetus, Norwalk, Conn.) using the following protocol. DNA denaturation steps were done by heating at 94° C. for 5 min. Thereafter, samples were run for 35 PCR cycles of denaturation (94° C. for 30 sec), primer annealing (60° C. for 30 sec), and chain extension (72° C. for 1 min) and the final extension time was extended for 7 min. The PCR products were checked by visualization on an agarose gel. Electrophoresis was with 20 μl of the amplified DNA on a 1.5% agarose gel containing 0.5 μg/ml ethidium bromide.

Infection/Transmission Experiments

To evaluate HIV infection/transmission in the in vitro generated cervico-vaginal tissue equivalent, the tissue was topically exposed to ADA (macrophage tropic) or NL4-3 (T-cell tropic) HIV-1 isolates (50,000 CPM/tissue) for 24 hr at 37° C. under the air-liquid interface condition, as schematically depicted in FIG. 1. After 24 hr, the residual virus on the surface of the tissue was washed 10 times with PBS and the tissue was continued in culture as follows:

a) Air-liquid interface (ALI): Virus-exposed tissue was fed through the membrane of the cell culture insert under the basolateral EC tissue surface. No T-cells were present in the medium.

b) Air-liquid interface+Jurkat cells (ALI+J): Same as a) with the addition of 1×10⁶ Jurkat cells to the medium beneath the cell culture insert. The membrane of the cell culture insert prevented any direct contact between the tissue and the Jurkat cells.

c) Submerged (SUB): Virus-exposed tissue was peeled off the tissue culture insert and submerged in medium containing 1×10⁶ Jurkat cells.

Culture medium samples were collected on days 3, 7, and 10, after topical washing to remove virus, and the reverse transcriptase assay was used to determine viral presence.

Results

The results are shown in Table 6.

TABLE 6

Infection of Langerhans cell-containing, cervico-vaginal tissue equivalent with macrophage tropic (ADA) and T-cell tropic (NL4-3) HIV-1 isolates. 50,000 CPM of virus were topically applied to the tissue. After 24 hours, the tissue was washed with PBS 10 times (Day 0), and cultures were continued under ALI, ALI + J, or SUB conditions, as described above. The degradation of the virus at 37° C. was also determined by incubating cell free virus (50,000 CPM) at 37° C. in a test tube.

| | | Reverse Transcriptase Values (CPM/ml) | | |
|---|---|---|---|---|
| Condition | Virus | Day 3 | Day 7 | Day 10 |
| ALI | ADA | 59 | 65 | 71 |
| | NL4-3 | 131 | 77 | 95 |
| ALI + J | ADA | 77 | 89 | 77 |
| | NL4-3 | 89 | 1341 | 3212 |
| SUB | ADA | 47 | 89 | 119 |
| | NL4-3 | 86 | 1977 | 22243 |
| Virus degradation (50,000) | | 689 | 154 | 137 |

No virus was detected in medium of the ALI culture. No virus was detected in medium of the ALI+J culture, indicating that there was no virus production/transmission by the macrophage tropic virus (ADA) to the T-cells added to the medium beneath the tissue. This was expected since macrophage tropic virus does not productively infect T-cells. However, when the T-cell tropic virus, NL4-3, was used, virus was detected in the medium of the ALI+J culture. This indicate that the virus was transmitted to the T-cells by the vaginal tissue. The presence of the membrane of the cell culture insert slowed but did not prevent virus transmission across the tissue.

These results suggest two possible mechanisms. The first possible mechanism is that the tissue was infected, and following infection, the virus was transmitted to the T-cells. An alternative mechanism is that the NL4-3 virus permeated into the tissue and associated thereto. This association protected the virus and prevented its degradation (Table 5). Eventually, though small amounts of live virus were released or permeated through the tissue (below the level of detection by RT), T-cells were infected, and large amounts of virus were produced by the T-cells. To determine which of these two possibilities was in fact occurring, cervico-vaginal tissue equivalent with and without Langerhans cells were infected (using the same protocol as used to generate the results of Table 5) and the DNA was extracted and analyzed using PCR. The products of the amplification reaction were size fractionated on a gel, and the presence or absence of HIV transcripts determined. Transcripts (around 400 bp in size) were observed in both Langerhans cell containing (LC+) and Langerhans cell-free (LC−) tissue for both the ADA (MT) and NL3-4 (TCT) viruses. As would be expected, more HIV transcripts were present in tissue exposed to ADA than NL4-3, and more transcripts were observed in LC+ cultures than in the LC− tissues. These results conclusively demonstrate that the pro-virol HIV DNA was incorporated into the genome of the tissue, indicating that infection of the tissue had indeed occurred. This indicates that the cervico-vaginal tissue equivalent is infectible by pathogens such as HIV, and can be used to study transmission of such pathogens and to analyze effectiveness of treatment or prevention thereof.

One of average skill in the art will recognize that many additional variations on the primary culture techniques not specifically referred to in this disclosure are possible in the successful generation of the cervico-vaginal tissue equivalent of the invention.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method for producing a cervico-vaginal tissue equivalent, comprising the steps:
   providing vaginal epithelial cells and immune cells;
   seeding the cells,
   co-cultivating the seeded cells submerged in growth medium under conditions appropriate for cell propagation; and
   co-culturing the seeded cells at the air-liquid interface under conditions appropriate for differentiation.

2. The method of claim 1 wherein the growth medium of the co-cultivating step is serum free growth medium.

3. The method of claim 1 further comprising the step of culturing the vaginal epithelial cells submerged in growth medium under conditions appropriate for cell propagation, prior to the seeding step.

4. The method of claim 1 further comprising the step of further seeding additional immune cells into the co-cultured seeded cells after the co-culturing step, and further co-culturing the seeded cells at the air liquid interface, under conditions appropriate for differentiation.

5. The method of claim 1 wherein the co-culturing step is in serum free differentiation medium.

6. The method of claim 1 wherein the vaginal epithelial cells or the immune cells, or both, of the providing step, are selected from the group consisting of primary cells, passaged primary cells, transformed cells, and immortalized cells.

7. The method of claim 6 wherein the primary or passaged primary vaginal epithelial cells of the providing step are derived from tissue selected from the group consisting of normal human ectocervical tissue, normal human endocervical tissue, pathological human ectocervical tissue, and pathological human endocervical tissue.

8. The method of claim 1 wherein the immune cells comprise Langerhans cells, Langerhans precursor cells (CD34+), monocytes (CD14+), immature dendritic cells (CD1a+, CD4+), mature dendritic cells (CD86+, HLA-DR++), T cells CD3+), macrophages, or any combination thereof.

9. The method of claim 1 further comprising the step of generating the immune cells for the providing step in vitro from harvested $CD34^+$ cells, prior to the providing step.

10. The method of claim 9 wherein the step of generating the immune cells from harvested CD34+ cells, comprises the steps:
    harvesting CD34+ cells from human umbilical cord blood, peripheral blood or bone marrow;
    initially culturing the CD34+ cells in medium comprising 25 ng/ml stem cell factor, about 200 U/ml GM-CSF, and about 2.5 ng/ml TNF-α, for a period of from about 1 to about 10 days; and
    continuing culturing the CD34+ cells in medium comprising about 25 ng/ml stem cell factor, about 200 U/ml GM-CSF, about 40 ng/ml IL-4, and about 0.5 ng/ml TGF-β1 for a period of from about 1 to about 17 days;
    to thereby generate the immune cells.

11. The method of claim 10 wherein the period of the initially culturing step is about 7 to about 9 days.

12. The method of claim 10 wherein the period of the continuing culturing step is about 5 to about 10 days.

13. The method of claim 9 wherein the step of generating the immune cells from harvested CD34+ cells, comprises the steps:
    harvesting CD34+ cells from human umbilical cord blood, peripheral blood or bone marrow;
    initially culturing the CD34+ cells in serum free medium comprising about 20 ng/ml stem cell factor, about 500 U/ml GM-CSF, and about 2.5 ng/ml TNF-α, for a period of at least about 4 days;
    continuing culturing the CD34+ cells in serum free medium comprising about 20 ng/ml stem cell factor, about 500 U/ml GM-CSF, about 2.5 ng/ml TNF-α, about 20 ng/ml FLT-3, and about 0.5 ng/ml TGF-β1, for a period of at least about 5 days; and
    further culturing the CD34+ cells in serum free medium comprising about 20 ng/ml stem cell factor, about 500 U/ml GM-CSF, about 40 ng/ml IL-4, about 20 ng/ml FLT-3, and about 0.5 ng/ml TGF-β1, for a period of at least about 3 days;
    to thereby generate the immune cells.

14. The method of claim 1 wherein the seeding step is on an underlying support selected from the group consisting of an artificial membrane, an extracellular matrix component, a collagen mixture, in vivo derived connective tissue, a mixed collagen-fibroblast lattice, mixed extracellular matrix-fibroblast lattice, and plastic.

15. The method of claim 14 wherein the mixed collagen-fibroblast lattice is comprised of vaginal fibroblasts.

16. The method of claim 15 wherein the mixed collagen-fibroblast lattice is further comprised of T cells (CD3+).

17. The method of claim 1 wherein the vaginal epithelial cells or the immune cells, or both, of the providing step, are of human origin.

18. The method of claim 1 wherein the immune cells of the providing step are generated from Langerhans precursor cells or monocytes.

19. The method of claim 1 further comprising isolating the immune cells for the providing step as immature or mature dendritic cells, prior to the providing step.

20. The method of claim 1 wherein the co-culturing step is in differentiation medium comprising a retinoid.

21. The method of claim 20 wherein the differentiation medium comprises between about $10^{-5}$ M and about $10^{-13}$ M of the retinoid.

22. The method of claim 21 wherein the retinoid is retinoic acid.

23. The method of claim 22 wherein the concentration of retinoic acid is about $5 \times 10^{-10}$ M.

24. The method of claim 23 wherein the differentiation medium is serum free medium, comprising:
    a) about a 3:1 ratio of DMEM:F12; and
    b) about $5 \times 10^{-10}$ M retinoic acid.

25. The method of claim 24 wherein the serum-free differentiation medium further comprises about 0.3 ng/ml keratinocyte growth factor, about 5 ng/ml EGF, about 0.4 μg/ml hydrocortisone, and about 5 μg/ml insulin.

26. The method of claim 1 wherein the co-culturing step is in differentiation medium comprising at least one component selected from the group consisting of adenine, α-melanocyte stimulating hormone, arachidonic acid, β-fibroblast growth factor, bovine pituitary extract, bovine serum albumin, calcium chloride, calf serum, carnitine, cholera toxin, dibutyl cyclic adenosine monophosphate, endothelin-1, epidermal growth factor, epinephrine, estradiol, estrogen, ethanolamine, fetal bovine serum, FLT-3, glucagon, granulocyte/macrophage-colony stimulating factor, hepatocyte growth factor, horse serum, human serum, hydrocortisone, insulin, insulin-like growth factor 1, insulin-like growth factor 2, interleukin-1β, interleukin-3, interleukin-4, interleukin-6, interleukin-12, interleukin-18, iso-butyl methyl xanthine, isoproterenol, keratinocyte growth factor, linoleic acid, MIP-1α, MIP-3α, newborn calf serum, nor-epinephrine, oleic acid, palmitic acid, phosphoethanolamine, progesterone, stem cell factor, transferrin, transforming growth factor-β1, triidothyronine, tumor necrosis factor α, vitamin A, vitamin B12, vitamin C, vitamin D, and vitamin E.

27. The method of claim 1 wherein from about $1\times10^3$ to about $1\times10^7$ cells/cm$^2$ of each cell type are seeded in the seeding step.

28. The method of claim 27 wherein from about $1\times10^5$ to about $1\times10^6$ cells/cm$^2$ of each cell type are seeded in the seeding step.

29. The method of claim 1 wherein the seeding step is at a ratio of about 1:1 vaginal epithelial cells to immune cells.

30. The method of claim 1 wherein the seeding step is at a ratio of between about 1:1 and 10,000:1 vaginal epithelial cells to immune cells, and the co-culturing step is in serum-free medium supplemented with additives which increase viability or induce proliferation of the immune cells.

31. The method of claim 30 wherein the ratio is from about 20:1 to about 50:1 vaginal epithelial cells to immune cells.

* * * * *